(12) United States Patent
Schultz

(10) Patent No.: US 9,386,824 B1
(45) Date of Patent: Jul. 12, 2016

(54) SECURE STRAP SYSTEMS

(71) Applicant: Joseph P. Schultz, Atlanta, GA (US)

(72) Inventor: Joseph P. Schultz, Atlanta, GA (US)

( * ) Notice: Subject to any disclaimer, the term of this patent is extended or adjusted under 35 U.S.C. 154(b) by 235 days.

(21) Appl. No.: 13/765,168

(22) Filed: Feb. 12, 2013

Related U.S. Application Data

(63) Continuation-in-part of application No. 12/548,377, filed on Aug. 26, 2009, now Pat. No. 8,371,000, which is a continuation-in-part of application No. 11/670,829, filed on Feb. 2, 2007, now Pat. No. 7,587,796, which is a continuation-in-part of application No. 10/465,162, filed on Jun. 18, 2003, now abandoned, which is a continuation-in-part of application No. 10/094,524, filed on Mar. 7, 2002, now abandoned.

(60) Provisional application No. 60/274,033, filed on Mar. 7, 2001.

(51) Int. Cl.
*A44B 18/00* (2006.01)
*B65D 63/10* (2006.01)

(52) U.S. Cl.
CPC .......... *A44B 18/0069* (2013.01); *A44B 18/003* (2013.01); *A44B 18/0019* (2013.01); *A44B 18/0042* (2013.01); *A44B 18/0084* (2013.01); *B65D 63/10* (2013.01); *B65D 2313/02* (2013.01); *Y10T 24/2708* (2015.01); *Y10T 24/2775* (2015.01)

(58) Field of Classification Search
CPC ............ Y10T 24/2708; Y10T 24/2775; A44B 18/0042; A44B 18/0019; A44B 18/003; A44B 18/0084
See application file for complete search history.

(56) References Cited

U.S. PATENT DOCUMENTS

| | | | |
|---|---|---|---|
| 1,202,971 A | 10/1916 | Diaber | |
| 3,251,069 A | 5/1966 | Clark | |
| 3,648,968 A | 3/1972 | Reid et al. | |
| 3,680,560 A | 8/1972 | Pannier, Jr. et al. | |
| 3,947,927 A | 4/1976 | Rosenthal | |
| 4,088,136 A | 5/1978 | Hasslinger et al. | |
| 4,114,838 A | 9/1978 | Knauf | |
| D251,121 S | 2/1979 | Smith | |
| 4,215,687 A | 8/1980 | Shaw | |
| 4,273,126 A | 6/1981 | Grane et al. | |
| 4,534,542 A | 8/1985 | Russo | |
| 4,617,017 A | 10/1986 | Hubbard et al. | |
| 4,766,682 A | 8/1988 | Malloy, III | |
| 4,805,611 A | 2/1989 | Hodgkins | |
| 4,856,149 A | 8/1989 | Brame | |
| 4,872,579 A | 10/1989 | Palmer | |
| 4,909,051 A | 3/1990 | Lee | |
| 4,915,691 A | 4/1990 | Jones et al. | |
| 5,048,158 A | 9/1991 | Koerner | |
| 5,098,416 A | 3/1992 | Imonti | |
| 5,168,603 A * | 12/1992 | Reed | 24/306 |

(Continued)

FOREIGN PATENT DOCUMENTS

WO     WO9112033 A1     8/1991

*Primary Examiner* — Robert J Sandy
(74) *Attorney, Agent, or Firm* — Merchant & Gould P.C.

(57) ABSTRACT

A strap system for selectively and independently binding and/or releasing at least one sets of essentially longitudinal objects, such as wires, from one another. A continuous strip of such two-sided material may be stored on a reel and is designed so that a user may select a preferred length and configuration for a particular use by making a single cut of the material strip from the reel-strip end.

16 Claims, 8 Drawing Sheets

(56) References Cited

U.S. PATENT DOCUMENTS

| | | | |
|---|---|---|---|
| 5,256,160 A | 10/1993 | Clement | |
| 5,292,312 A | 3/1994 | Delk et al. | |
| 5,335,655 A | 8/1994 | Kee | |
| 5,336,172 A | 8/1994 | Bales et al. | |
| 5,395,018 A | 3/1995 | Studdiford | |
| 5,433,195 A | 7/1995 | Kee et al. | |
| 5,460,308 A | 10/1995 | Hahn | |
| 5,548,871 A | 8/1996 | Trethewey | |
| 5,549,585 A | 8/1996 | Maher et al. | |
| 5,562,077 A | 10/1996 | Schultz | |
| 5,769,290 A | 6/1998 | Pestana | |
| 5,785,011 A | 7/1998 | Gitterman, III | |
| 5,802,676 A | 9/1998 | Tolan | |
| 5,819,391 A * | 10/1998 | Matsushima et al. | 24/452 |
| 6,279,168 B1 | 8/2001 | Bean | |
| 6,317,933 B1 | 11/2001 | Suenaga | |
| 6,346,075 B1 | 2/2002 | Arai et al. | |
| 6,368,310 B1 | 4/2002 | Bemis et al. | |
| 6,415,823 B1 | 7/2002 | Vasek et al. | |
| 6,471,680 B1 | 10/2002 | Cawood | |
| 6,484,371 B1 * | 11/2002 | Romanko et al. | 24/306 |
| 6,490,767 B2 | 12/2002 | Haiduk | |
| 6,543,159 B1 | 4/2003 | Carpenter | |
| 6,588,074 B2 | 7/2003 | Galkiewicz et al. | |
| 6,701,580 B1 * | 3/2004 | Bandyopadhyay | 24/306 |
| 6,770,063 B2 | 8/2004 | Goldberg et al. | |
| 6,775,896 B2 * | 8/2004 | Dudek et al. | 29/417 |
| 6,890,323 B1 | 5/2005 | Antonelli | |
| 8,413,306 B2 * | 4/2013 | Gallant et al. | 24/306 |
| 2002/0108614 A1 | 8/2002 | Schultz | |
| 2002/0143323 A1 | 10/2002 | Johnston et al. | |
| 2003/0110596 A1 * | 6/2003 | Graham et al. | 24/16 R |
| 2003/0150087 A1 * | 8/2003 | Dieterich | 24/306 |
| 2005/0217087 A1 * | 10/2005 | Gallant | 24/452 |

\* cited by examiner

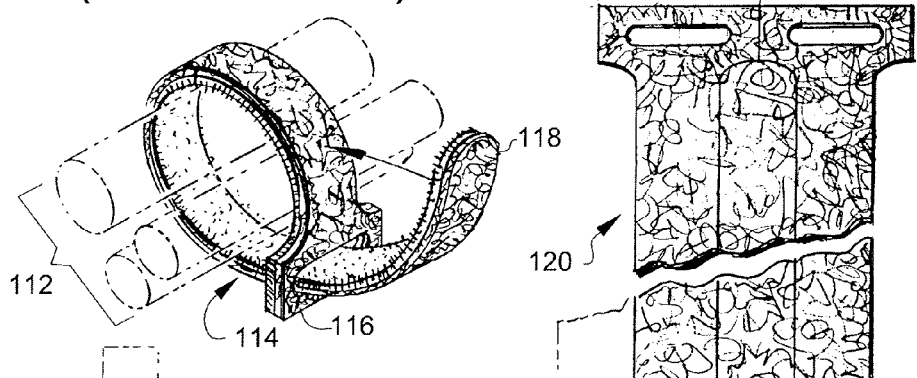
FIG. 1 (PRIOR ART)
FIG. 2 (PRIOR ART)
FIG. 3
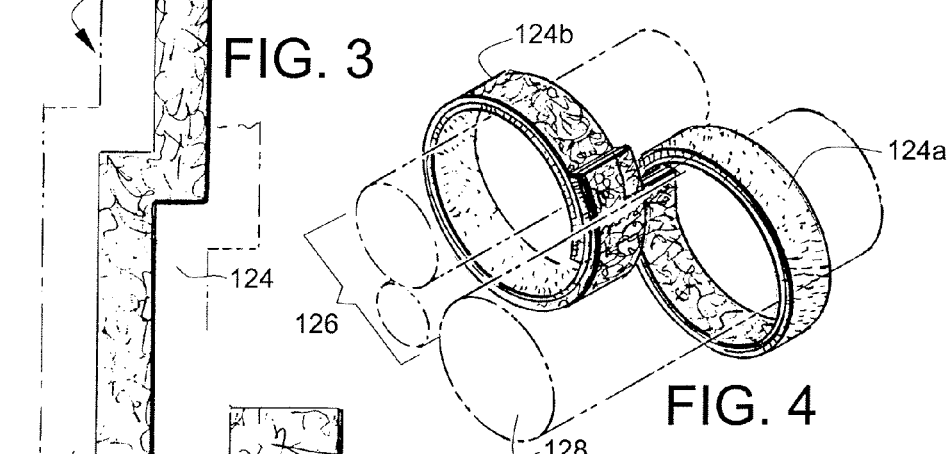
FIG. 4
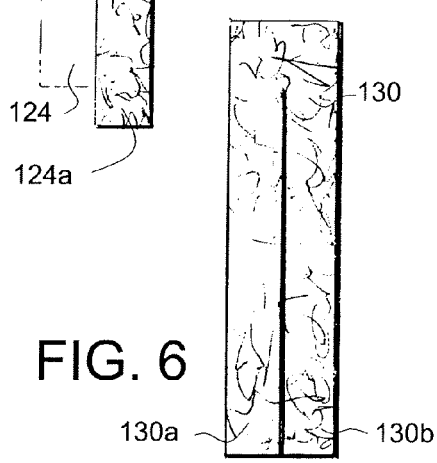
FIG. 6
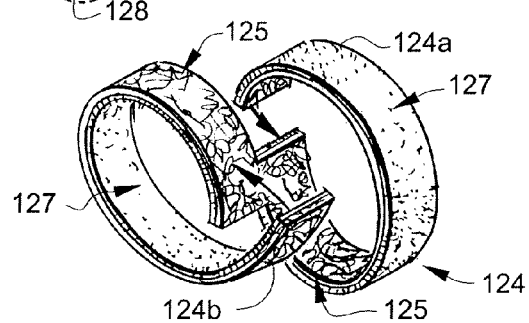
FIG. 5

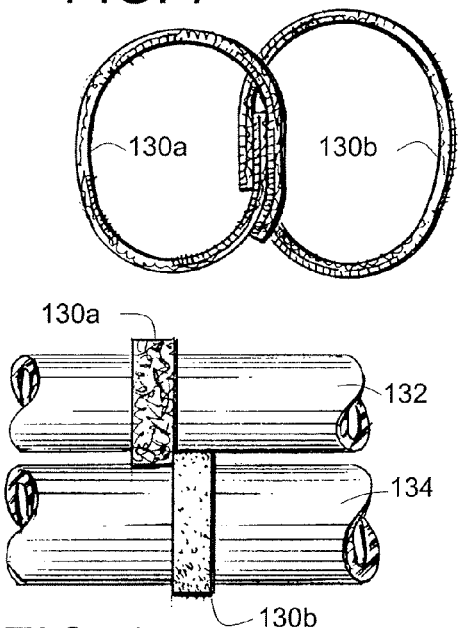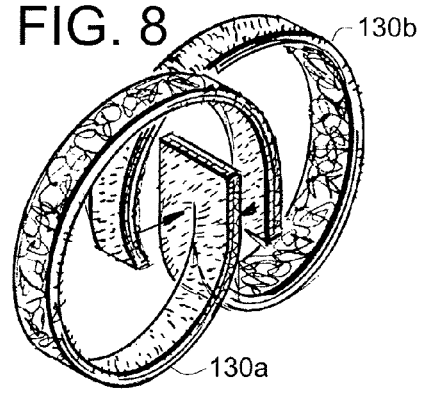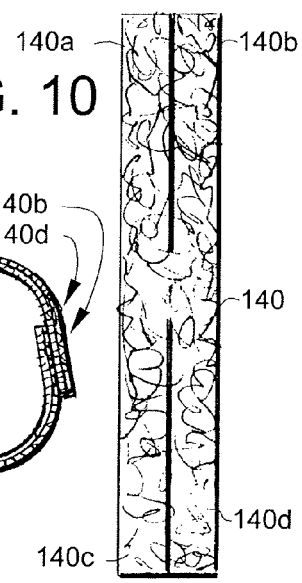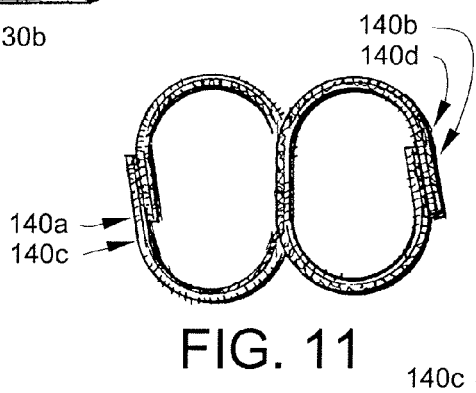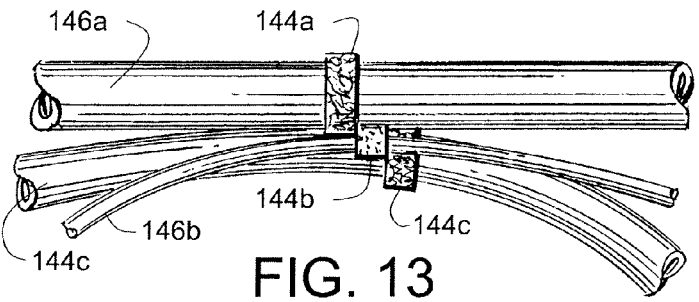

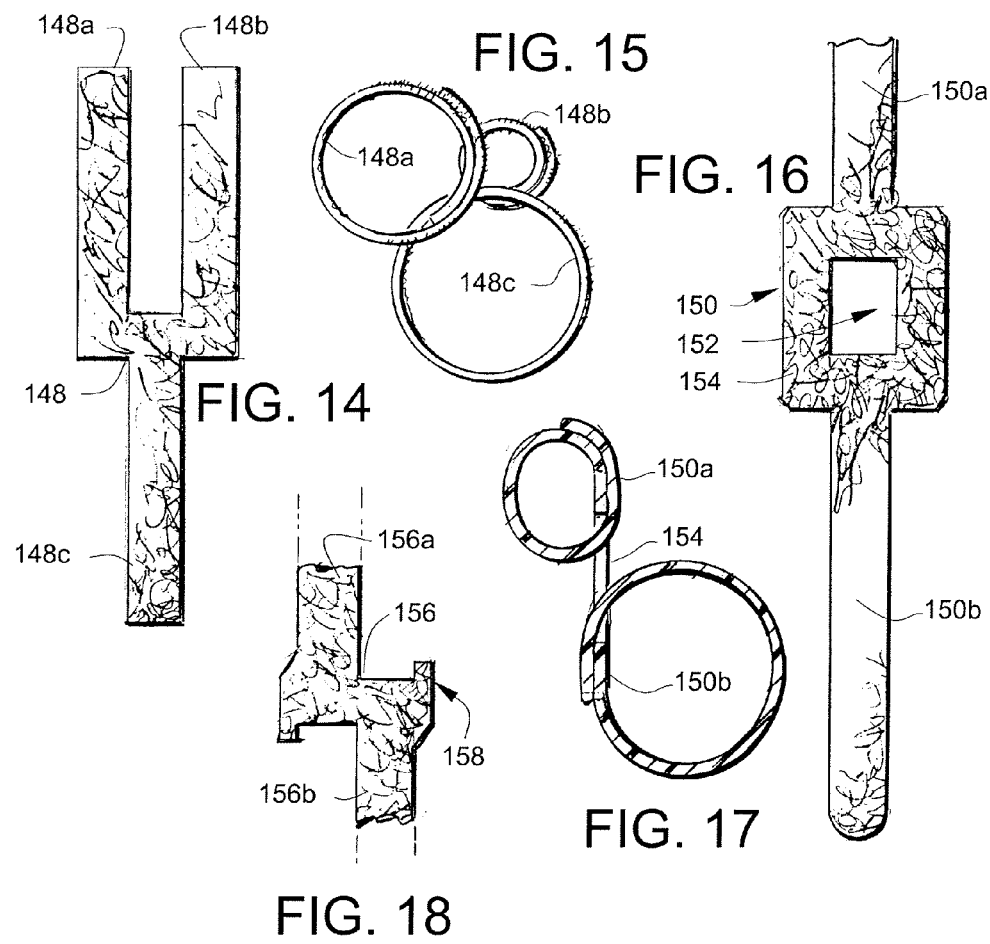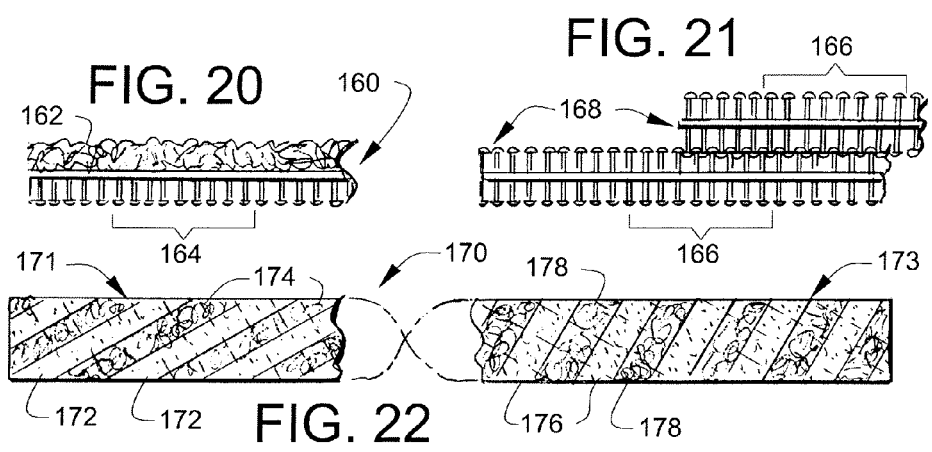

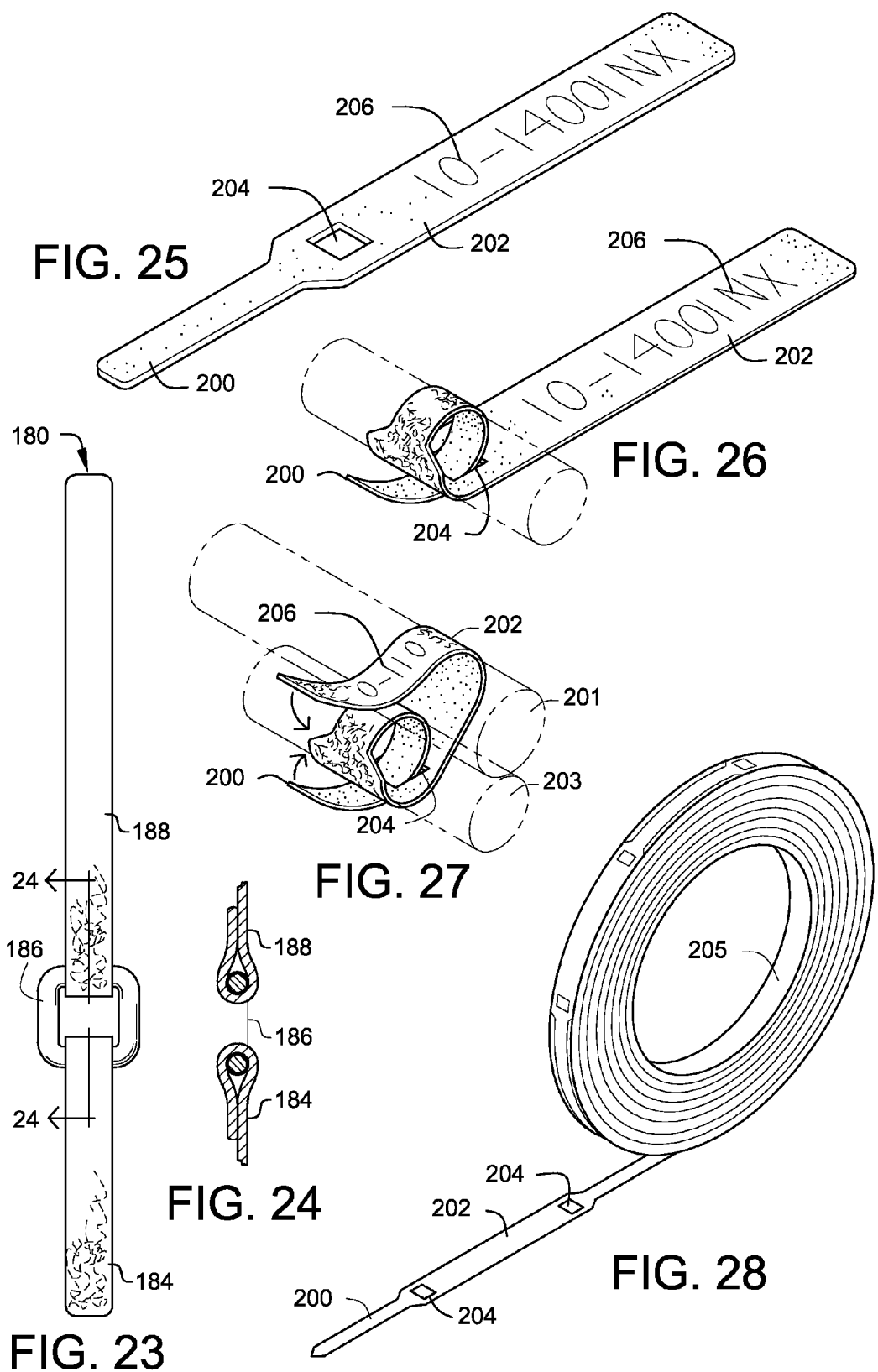

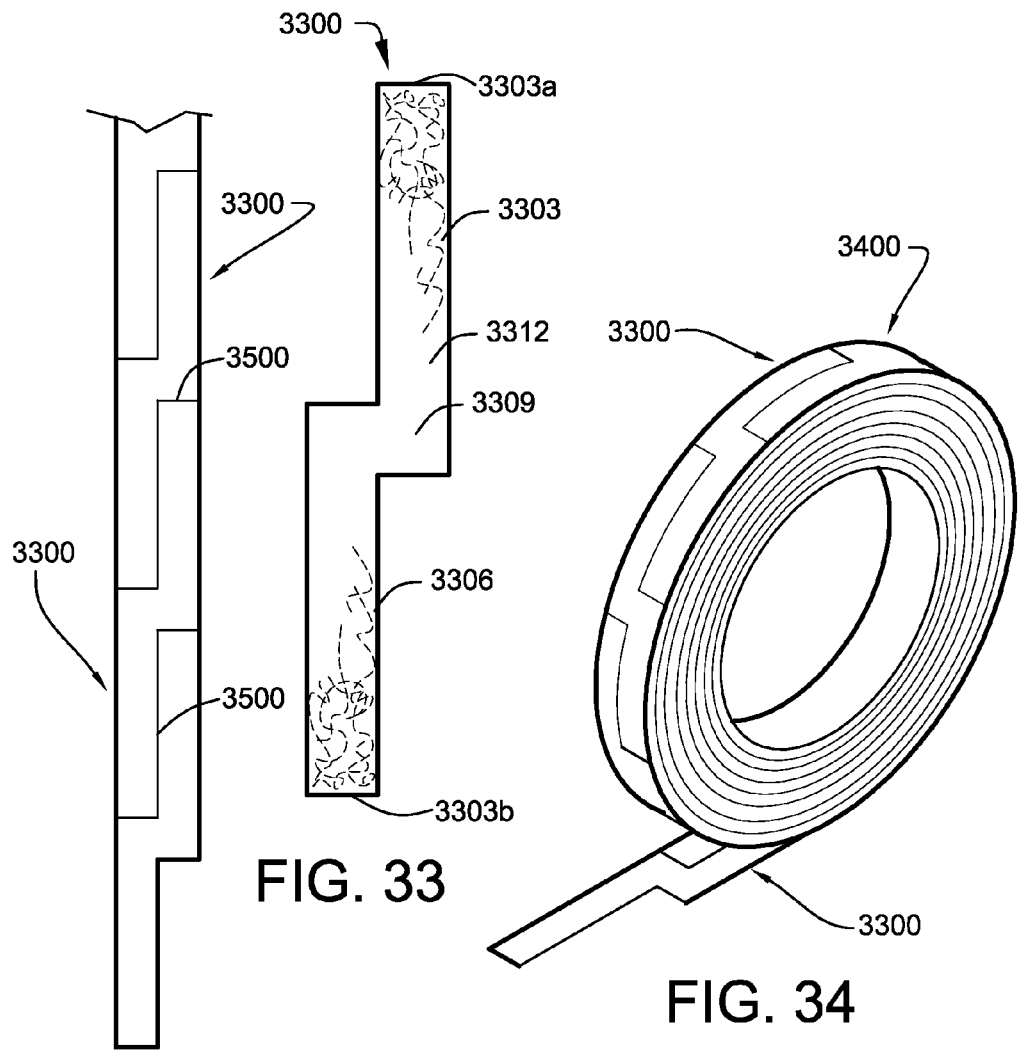
FIG. 33
FIG. 34
FIG. 35
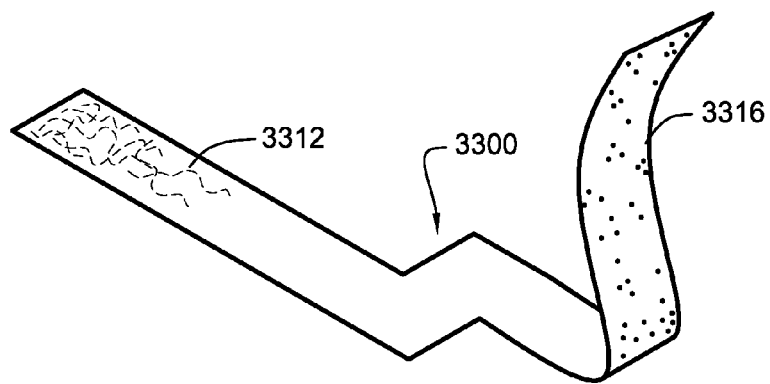
FIG. 36

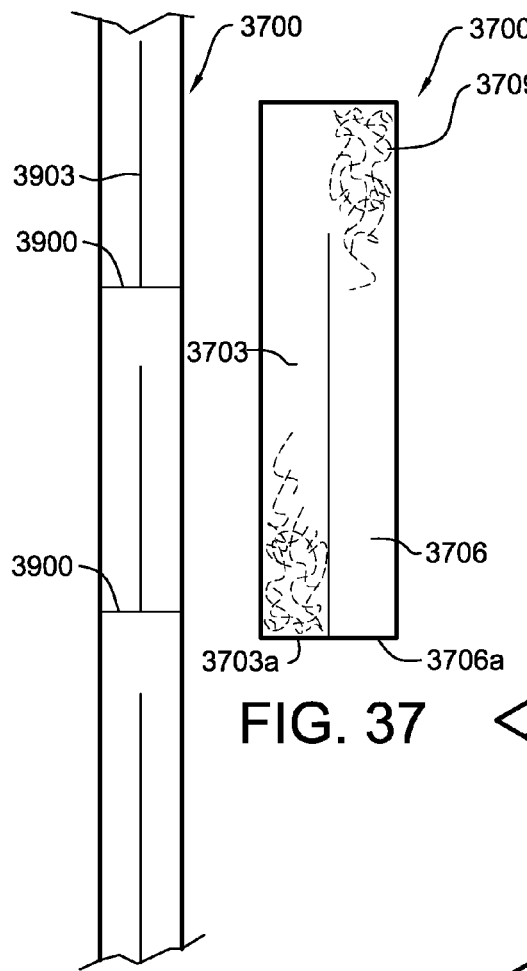
FIG. 37
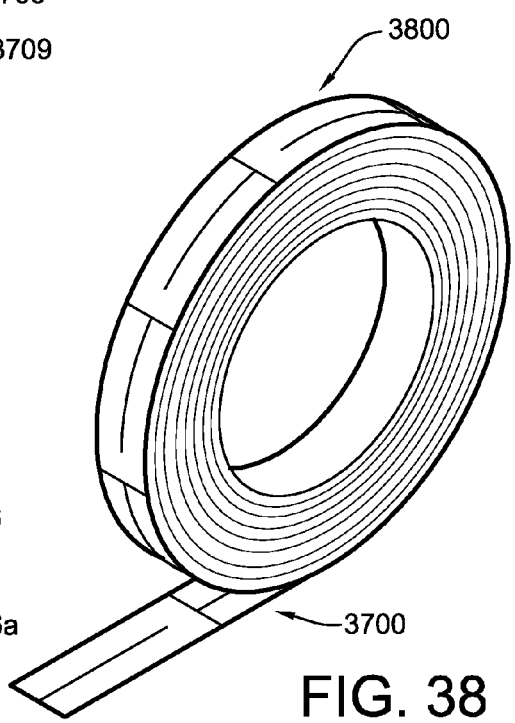
FIG. 38
FIG. 39
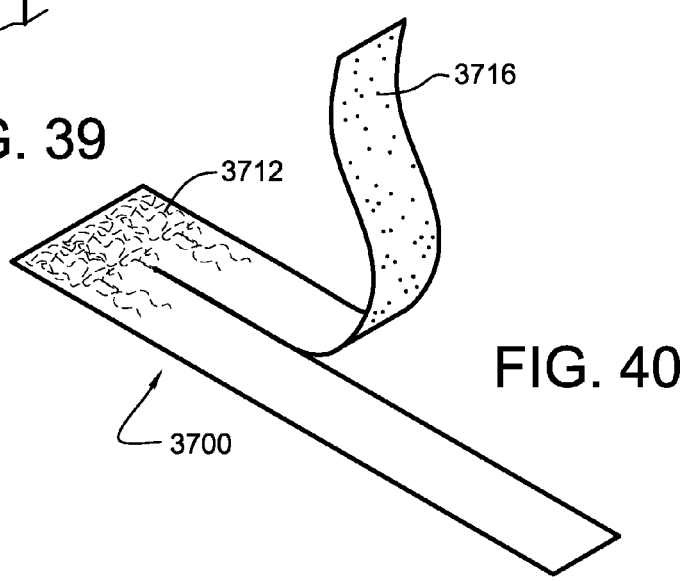
FIG. 40

SECURE STRAP SYSTEMS

CROSS-REFERENCE TO RELATED APPLICATIONS

The present application is a continuation-in-part of related patent application Ser. No. 12/548,377, filed Aug. 26, 2009, entitled "SECURE STRAP SYSTEMS", which is a continuation-in-part of related patent application Ser. No. 11/670,829, filed Feb. 2, 2007, entitled "SECURE STRAP SYSTEMS", which is a continuation-in-part of related patent application Ser. No. 10/465,162, filed Jun. 18, 2003, entitled "LOOPABLE, SECURE MULTIPLE-FASTENING-STRAP SYSTEMS", which is a continuation-in-part of related application Ser. No. 10/094,524, filed Mar. 7, 2002, entitled "FASTENING STRAP SYSTEM", which is related to and claims priority from prior provisional patent application Ser. No. 60/274,033, filed Mar. 7, 2001, entitled "FASTENING STRAP SYSTEM", the contents all of which are incorporated herein by this reference and are not admitted to be prior art with respect to the present invention by mention is this cross-reference section.

BACKGROUND

This invention relates to fastening strap systems. More particularly, it relates to such strap systems, using fastenable and releasable materials (such as VELCRO® fasteners), as may be suited for the securing together of more than one bundle or set of elongated items such as cables, wires, pens, skis, pipe, tent poles, boards, angle iron, golf clubs, etc., and/or tying down such bundle(s) by securing such to an "anchor" such as a computer or table leg, etc.

When addressing the fastening or securing of bundles of substantially elongated items such as cables, wires, pens, skis, pipe, tent poles, boards, angle iron, golf clubs, etc., a need exists to securely fasten all the items to each other in a bundle while still allowing for the selective release of certain members of the bundle. While generic tying or binding materials exist, such as string, tape, etc., these materials have many drawbacks related to tape glue residue, the thin material of the material causing cuts into the bound items, and a lack of selective fastening and/or release. Although some fastening systems exist that utilize hook and loop material, some problems remain. FIG. 1 and FIG. 2 show a prior art fastening strap.

Velcro USA, Inc., makes a fastener material, which is a double-sided material with fastening hooks on one surface and fastening loops on the opposite surface, as shown in FIG. 2. This fastener material is marketed by Velcro USA, Inc., under the names GET A GRIP® and ONE WRAP®. The GET A GRIP® straps provide a strap with an aperture at one end and with a pulling end at the other end that allows a user to pull on the free end of the strap and cinch a bundle prior to fastening the hook and loop surfaces together. An example of such a strap might be similar to the strap illustrated in FIGS. 1 and 2, which show respectively: a prior art fastening strap 114 with a pulling end 118 and aperture end 116, wrapped around a bundle 112; and a sheet 120 of double-sided fastening strap material apportioned for die cut manufacturing of the fastening straps.

There are however, undesirable limitations to this prior art. For example, the pulling end 118 of the GET A GRIP® strap has the disadvantage of being extremely short, and thus it is practically incapable of bundling another object to a first object.

Given a desire to integrally connect a first set of bundled objects A to a second set B of bundled objects, there is a need for a fastening strap system that permits tightly cinching the first set of objects to achieve a better total fit around all the bundled A and B sets of objects. Furthermore, it would be desirable to have a fastening strap system that can fasten both a set A and a set B (in a manner not conducive to "normal" loosening by "normal" forces) but then allow the release of either set A or set B while leaving the remaining set fastened intact, which could then be immediately attachable to a third set C. In addition, it would be desirable to have a secure fastening strap system that could release either of two fastened sets, e.g., a cord bundle and its plug, independently at will. Further, it would be desirable to have an improved fastening strap system for securing two items or sets of items together which allows separation of either set immediately with a minimum of manipulation while also maintaining a relatively strong fastening grip when fastened.

Also, it would be desirable to have a self-fastening strap, made of a self-fastening material such as hook and loop material, which could be anchored with relative ease without having to unwind the entire strap or unbundle and unwind the entire strap, or which, with relatively less problems of tangling and prematurely self-fastening, could be easily accomplished by a single hand. Another desirable feature would be to have a self-fastening strap, made of a self-fastening material, such as hook and loop material, which could be released without having to unbundle and unwind the entire strap or which might be released easily from an anchored position with a single hand. It would also be desirable, among a long list of associated needs, to provide a better method of manufacture of fastening strap systems which include desired features and to provide better methods of dispensing, packaging, and use of such fastening strap systems.

OBJECTS OF THE INVENTION

It is a primary object and feature of this invention to fulfill the above-mentioned needs and the other needs apparent from the discussion of this specification. Another object and feature of the present invention is to provide a fastening strap system that can be used efficiently and effectively as an adjustable belt or strap without significant material design changes or functional limitations. It is another object and feature of the present invention to provide such a fastening strap system that provides for the selective and independent binding and release of multiple bundles of items from one another. It is another object and feature of the present invention to provide such a fastening strap system that is less likely to unintentionally come undone.

It is yet another object and feature of the present invention to provide such a fastening strap system that can be easily anchored. It is yet another object and feature of the present invention to provide such a system that can be used to label the bundled object(s). Another object and feature of the present invention is to provide such a fastening strap system that can be tailored by a user to fit different applications. It is yet another object and feature of the present invention is to provide such a fastener system that is efficiently and inexpensively manufactured and efficient to use.

The foregoing and other objects, features, and advantages of the present invention will be apparent from the following, more particular, description of the embodiments of the invention, as illustrated in the accompanying drawings.

SUMMARY OF THE INVENTION

In accordance with a preferred embodiment hereof, this invention provides a strap system utilized to secure at least one first longitudinal element and at least one second longitudinal element, comprising the steps of: providing at least one fastening strap system comprising at least one first elongated strap portion comprising at least one first strap end portion and at least one first strap width, and at least one second elongated strap portion comprising at least one second strap end portion and at least one second strap width, wherein such fastening strap system consists essentially of a unitary portion of flexible sheet material, wherein such unitary portion of flexible sheet material comprises at least one first side comprising at least one first fastening surface and at least one second side comprising at least one second fastening surface adapted to be detachably fastenable to such at least one first fastening surface, wherein such second elongated strap portion is offset parallel from such first elongated strap portion a distance about equal to such at least one first strap width, and wherein all such at least one first elongated strap portions and all such at least one second elongated strap portions are parallel; folding such at least one first elongated strap portion around the at least one first longitudinal element; folding such at least one second elongated strap portion around the at least one second longitudinal element; cinching such at least one first elongated strap portion; and cinching such at least one second elongated strap portion.

Moreover, it provides such a system, wherein: such step of folding such at least one first elongated strap portion around the at least one first longitudinal element comprises the step of looping such at least one first elongated strap portion clockwise around the at least one first longitudinal element; and such step of folding such at least one second elongated strap portion around the at least one second longitudinal element comprises the step of looping such at least one second elongated strap portion counter-clockwise around the at least one second longitudinal element.

Additionally, it provides such a system, wherein: such step of folding such at least one first elongated strap portion around the at least one first longitudinal element comprises creating at least one first loop around the at least one first longitudinal element comprising folding, in a clockwise direction, such at least one first elongated strap portion around the at least one first longitudinal element and cinching such at least one first elongated strap portion; and such step of folding such at least one second elongated strap portion around the at least one second longitudinal element comprises creating at least one second loop around the at least one second longitudinal element, wherein such at least one second loop is offset from such at least one first loop by a distance about equal to such at least one first strap width, folding, in a counterclockwise direction, such at least one second elongated strap portion around the at least one second longitudinal element, and cinching such at least one second elongated strap portion.

In accordance with another preferred embodiment hereof, this invention provides a system comprising: a first plurality of detachable fasteners; at least one first detachable-fastener surface structured and arranged to hold such first plurality of detachable fasteners; a second plurality of detachable fasteners; and at least one second detachable-fastener surface structured and arranged to hold such second plurality of detachable fasteners; wherein such at least one first detachable-fastener surface and such at least one second detachable-fastener surface comprise at least one unitary portion of flexible sheet material; wherein such at least one first detachable-fastener surface and such at least one second detachable-fastener surface are on different sides of such at least one unitary portion of flexible sheet material; and wherein such first plurality of detachable fasteners comprises at least one three-dimensional mushroom geometry.

Also, it provides such a system wherein such second plurality of detachable fasteners comprises at least one three-dimensional mushroom geometry. In addition, it provides such a system further comprising: at least one first elongated strap portion comprising at least one first strap end portion, and at least one first strap width; and at least one second elongated strap portion comprising at least one second strap end portion; and at least one second strap width. And, it provides such a system wherein such second elongated strap portion is offset parallel from such first elongated strap portion a distance about equal to such at least one first strap width.

Further, it provides such a system wherein such at least one first detachable-fastener surface substantially covers all of at least one first side of such at least one unitary portion of flexible sheet material. Even further, it provides such a system wherein such at least one second detachable-fastener surface substantially covers all of at least one second side of such at least one unitary portion of flexible sheet material. Moreover, it provides such a system wherein such at least one second detachable-fastener surface is adapted to be detachably fastenable to such at least one first detachable-fastener surface.

Additionally, it provides such a system wherein such second plurality of detachable fasteners comprises loops. Also, it provides such a system wherein such second plurality of detachable fasteners comprises hook fasteners. In addition, it provides such a system wherein such second plurality of detachable fasteners comprises mushroom-shaped hook fasteners.

In accordance with another preferred embodiment hereof, this invention provides a system comprising: a first plurality of detachable fasteners; at least one first detachable-fastener surface structured and arranged to hold such first plurality of detachable fasteners; a second plurality of detachable fasteners; and at least one second detachable-fastener surface structured and arranged to hold such second plurality of detachable fasteners; wherein such at least one first detachable-fastener surface and such at least one second detachable-fastener surface comprise at least one unitary portion of flexible sheet material; wherein such at least one first detachable-fastener surface and such at least one second detachable-fastener surface are on different sides of such at least one unitary portion of flexible sheet material; and wherein such first plurality of detachable fasteners comprises at least one bio-absorbable material.

And, it provides such a system wherein such second plurality of detachable fasteners comprises hook fasteners. Further, it provides such a system wherein such second plurality of detachable fasteners comprises mushroom-shaped hook fasteners. Even further, it provides such a system wherein such first plurality of detachable fasteners comprises hook fasteners. Even further, it provides such a system wherein such at least one second detachable-fastener surface is adapted to be detachably fastenable to such at least one first detachable-fastener surface. Even further, it provides such a system wherein such at least one second detachable-fastener surface is adapted to be detachably fastenable to such at least one first detachable-fastener surface. Even further, it provides such a strap system wherein such at least one bio-absorbable material comprises polylactic acid.

In accordance with another preferred embodiment hereof, this invention provides a fastening strap system relating to securing at least two elements, consisting of: at least one first strap portion having at least one first strap end portion, at least one first strap length, at least one first strap width; and at least one second strap portion having at least one second strap end portion, at least one second strap length, and at least one second strap width; wherein such at least one first strap portion has, at least one first side comprising at least one first fastening surface covering substantially all of such at least one first side, and at least one second side comprising at least one second fastening surface covering substantially all of such at least one second side, wherein such at least one first fastening surface is structured and arranged to be detachably fastenable to such at least one second fastening surface; wherein such at least one second strap portion is offset parallel from such first strap portion a distance about equal to such at least one first strap width; wherein all such at least one first strap portions and all such at least one second strap portions are parallel.

In accordance with another preferred embodiment hereof, this invention provides a fastening strap system relating to securing at least two elements, consisting of: at least one first strap portion comprising, at least one first strap end portion, at least one first strap length, at least one first strap width; and at least one second strap portion comprising, at least one second strap end portion, at least one second strap length, and at least one second strap width; at least one joining strap portion joining such at least one first strap portion and such at least one second strap portion; wherein such at least one first strap portion comprises, at least one first side comprising at least one first fastening surface covering substantially all of such at least one first side, and at least one second side comprising at least one second fastening surface covering substantially all of such at least one second side, wherein such at least one first fastening surface is structured and arranged to be detachably fastenable to such at least one second fastening surface; wherein such at least one second strap portion is offset parallel from such first strap portion a distance about equal to such at least one first strap width; wherein all such at least one first strap portions and all such at least one second strap portions are parallel. Moreover, it provides such a fastening strap system wherein, when such fastening strap system is laid flat, such at least one first strap end portion and such at least one second strap end portion are opposite one another relative to such at least one joining strap portion. Additionally, it provides such a fastening strap system wherein, when such fastening strap system is laid flat, such at least one first strap portion and such at least one second strap portion are structured and arranged such that a line and perpendicular to a longitudinal axis of such at least one first strap portion passing through such at least one first strap portion, but not passing through such at least one joining strap portion, also passes through such at least one second strap portion. Also, it provides such a fastening strap system wherein, when such fastening strap system is laid flat, such at least one first strap portion and such at least one second strap portion are structured and arranged such that a line perpendicular to a longitudinal axis of such at least one first strap portion passing through such at least one first strap portion, but not passing through such at least one joining strap portion, does not pass through such at least one second strap portion. In addition, it provides such a fastening strap system wherein such at least one first strap length and such at least one second strap length are equal. And, it provides such a fastening strap system wherein such at least one first strap width and such at least one second strap width are equal. Further, it provides such a fastening strap system wherein such at least one first strap width and such at least one second strap width are equal. Even further, it provides such a fastening strap system wherein such at least one joining strap portion comprises a joining strap width and such joining strap width is the widest portion of such fastening strap system. Moreover, it provides such a fastening strap system wherein such at least one first fastening surface comprises at least one hook fastening surface. Additionally, it provides such a fastening strap system wherein such at least one second fastening surface comprises at least one complementary hook fastening surface. Also, it provides such a fastening strap system wherein such at least one second fastening surface comprises at least one loop fastening surface.

In accordance with another preferred embodiment hereof, this invention provides a fastening strap system relating to securing at least two elements to be fastened, comprising: at least one continuous length of material comprising a plurality of removable portions; such at least one continuous length of material comprising at least one separation assister structured and arranged to assist removal of removable portions from such at least one continuous length of material; each removable portion comprising at least one first strap portion comprising, at least one first strap end portion, at least one first strap length, at least one first strap width; and at least one second strap portion comprising, at least one second strap end portion, at least one second strap length, and at least one second strap width; at least one joining strap portion joining such at least one first strap portion and such at least one second strap portion; wherein such at least one first strap portion comprises, at least one first side comprising at least one first fastening surface covering substantially all of such at least one first side, and at least one second side comprising at least one second fastening surface covering substantially all of such at least one second side, wherein such at least one first fastening surface is structured and arranged to be detachably fastenable to such at least one second fastening surface; wherein such at least one second strap portion is offset parallel from such first strap portion a distance about equal to such at least one first strap width; wherein all such at least one first strap portions and all such at least one second strap portions are parallel. In addition, it provides such a system wherein, when a removable portion is laid flat, such at least one first strap end portion and such at least one second strap end portion are opposite one another relative to such at least one joining strap portion. And, it provides such a system wherein, when a removable portion is laid flat, such at least one first strap portion and such at least one second strap portion are structured and arranged such that a line perpendicular to a longitudinal axis of such at least one first strap portion passing through such at least one first strap portion, but not passing through such at least one joining strap portion, also passes through such at least one second strap portion. Further, it provides such a system wherein, when a removable portion is laid flat, such at least one first strap portion and such at least one second strap portion are structured and arranged such that a line perpendicular to a longitudinal axis of such at least one first strap portion passing through such at least one first strap portion, but not passing through such at least one joining strap portion, does not pass through such at least one second strap portion. Even further, it provides such a system wherein such at least one separation assister comprises at least one perforation. Even further, it provides such a system wherein such at least one separation assister comprises multiple perforations. Even further, it provides such a system wherein such at least one separation assister comprises at least one line of perforations. Even further, it provides such a fastening strap system wherein such at least one first strap length and such at least one second strap length are equal. Even further, it provides such a fastening strap system wherein such at least one first strap width and such at least one second strap width are equal. Even further, it provides such a fastening strap system wherein such at least one first strap width and such at least one second strap width are equal. Even further, it provides such a fastening strap system wherein such at least one joining strap portion comprises at least one joining strap width and such at least one joining strap width is the widest portion of such fastening strap system. Even further, it provides such a fastening strap system wherein such at least one first fastening surface comprises at least one hook fastening surface. Even further, it provides such a fastening strap system wherein such at least one second fastening surface comprises at least one complementary hook fastening surface. Even further, it provides such a fastening strap system wherein such at least one second fastening surface comprises at least one loop fastening surface.

In accordance with a preferred embodiment hereof, this invention provides a fastening strap system, comprising: at least one first elongated strap portion comprising, at least one first strap end portion, and at least one first strap width; at least one second elongated strap portion comprising, at least one second strap end portion, and at least one second strap width; at least one aperture comprising, at least one aperture width, and at least one aperture length; wherein such fastening strap system consists essentially of a unitary portion of flexible sheet material; wherein such unitary portion of flexible sheet material comprises, at least one first side comprising at least one first fastening surface covering substantially all of such at least one first side, and at least one second side comprising at least one second fastening surface covering substantially all of such at least one second side adapted to be detachably fastenable to such at least one first fastening surface; wherein all such at least one first elongated strap portions and all such at least one second elongated strap portions are parallel and collinear; wherein such at least one aperture is located between such at least one first elongated strap portion and such at least one second elongated strap portion; and wherein such at least one aperture is structured and arranged to allow cinching such at least one first elongated strap portion.

In accordance with another preferred embodiment hereof, this invention provides a fastening strap system, comprising: at least one first elongated strap portion comprising, at least one first strap end portion, and at least one first strap width; and at least one second elongated strap portion comprising, at least one second strap end portion, and at least one second strap width; wherein such fastening strap system consists essentially of a unitary portion of flexible sheet material; wherein such unitary portion of flexible sheet material comprises, at least one first side comprising at least one first fastening surface covering substantially all of such at least one first side, and at least one second side comprising at least one second fastening surface covering substantially all of such at least one second side adapted to be detachably fastenable to such at least one first fastening surface; wherein such second elongated strap portion is offset parallel from such first elongated strap portion a distance about equal to such at least one first strap width; wherein all such at least one first elongated strap portions and all such at least one second elongated strap portions are parallel. Moreover, it provides such a strap system wherein such at least one first fastening surface comprises at least one hook fastening surface; and such at least one second fastening surface comprises at least one loop fastening surface. Additionally, it provides such a strap system wherein no elongated strap portion is perpendicular to such at least one first elongated strap portion; and no elongated strap portion is perpendicular to such at least one second elongated strap portion. Also, it provides such a strap system further comprising at least one third elongated strap portion comprising, at least one third strap end portion, and at least one third strap width; wherein such third elongated strap portion is offset parallel from such second elongated strap portion a distance about equal to such at least one second strap width.

In accordance with another preferred embodiment hereof, this invention provides a strap system, comprising: at least one first elongated strap portion comprising, at least one first strap end portion, and at least one first strap width; at least one second elongated strap portion comprising, at least one second strap end portion, and at least one second strap width; and at least one aperture comprising, at least one aperture width, and at least one aperture length; wherein such fastening strap system consists essentially of a unitary portion of flexible sheet material; wherein such unitary portion of flexible sheet material comprises, at least one first side comprising at least one first fastening surface, and at least one second side comprising at least one second fastening surface adapted to be detachably fastenable to such at least one first fastening surface; wherein all such at least one first elongated strap portions and all such at least one second elongated strap portions are parallel and collinear; wherein such at least one aperture is located between such at least one first elongated strap portion and such at least one second elongated strap portion; and wherein such at least one aperture is structured and arranged to allow cinching such at least one first elongated strap portion; wherein such at least one first fastening surface comprises at least one hook fastening surface; and wherein such at least one second fastening surface comprises at least one loop fastening surface. In addition, it provides such a strap system wherein such at least one first strap end portion is shorter than such at least one second strap end portion. And, it provides such a strap system wherein such at least one aperture comprises a portion devoid of such flexible sheet material. Further, it provides such a strap system wherein such at least one first strap width is not substantially greater than such at least one aperture width. Even further, it provides such a strap system wherein: such at least one first strap width is less than such at least one second strap width; such at least one aperture width is less than such at least one second strap width; and such at least one aperture is located within such at least one second elongated strap portion. Moreover, it provides such a strap system wherein such at least one first strap width is about equal to such at least one second strap width. Additionally, it provides such a strap system further comprising a plurality of such at least one apertures. Also, it provides such a strap system wherein such at least one first elongated strap portion comprises at least one label. In addition, it provides such a strap system wherein such at least one second elongated strap portion comprises at least one label. And, it provides such a fastening strap system wherein such at least one first side is substantially lighter in color than such at least one second side. Further, it provides such a strap system further comprising at least two such at least one apertures. Even further, it provides such a fastening strap system wherein such at least one second strap width is the widest portion of such fastening strap system.

In accordance with another preferred embodiment hereof, this invention provides a fastening strap system, comprising: at least one first elongated strap portion comprising, at least one first strap end portion, and at least one first strap width; at least one second elongated strap portion comprising, at least one second strap end portion, and at least one second strap width; and at least one aperture comprising, at least one aperture width, and at least one aperture length; wherein such fastening strap system consists essentially of a unitary portion of flexible sheet material; wherein such unitary portion of flexible sheet material comprises, at least one first side comprising at least one first fastening surface, and at least one second side comprising at least one second fastening surface adapted to be detachably fastenable to such at least one first fastening surface; wherein all such at least one first elongated strap portions and all such at least one second elongated strap portions are parallel and collinear; wherein such at least one aperture is located between such at least one first elongated strap portion and such at least one second elongated strap portion; wherein such at least one aperture is structured and arranged to allow cinching such at least one first elongated strap portion; wherein such at least one first strap width is less than such at least one second strap width; wherein such at least one aperture width is less than such at least one second strap width; wherein such at least one aperture is located within such at least one second elongated strap portion; wherein such at least one second strap width is the widest portion of such fastening strap system; and wherein such at least one first strap end portion is shorter than such at least one second strap end portion. Moreover, it provides such a fastening strap system wherein such at least one first strap end portion is at most half the length of such at least one second strap end portion. Additionally, it provides such a fastening strap system wherein such at least one first elongated strap portion comprises at least one label. Also, it provides such a fastening strap system wherein such at least one first side is substantially lighter in color than such at least one second side.

In accordance with another preferred embodiment hereof, this invention provides a method of using a fastening strap system utilized to secure at least one first longitudinal element and at least one second longitudinal element, comprising the steps of: providing at least one a fastening strap system comprising at least one first elongated strap portion comprising, at least one first strap end portion, and at least one first strap width; and at least one second elongated strap portion comprising, at least one second strap end portion, and at least one second strap width; wherein such fastening strap system consists essentially of a unitary portion of flexible sheet material; wherein such unitary portion of flexible sheet material comprises, at least one first side comprising at least one first fastening surface, and at least one second side comprising at least one second fastening surface adapted to be detachably fastenable to such at least one first fastening surface; wherein such second elongated strap portion is offset parallel from such first elongated strap portion a distance about equal to such at least one first strap width; wherein all such at least one first elongated strap portions and all such at least one second elongated strap portions are parallel; folding such at least one first elongated strap portion around the at least one first longitudinal element; folding such at least one second elongated strap portion around the at least one second longitudinal element; cinching such at least one first elongated strap portion; and cinching such at least one second elongated strap portion. In addition, it provides such a method, wherein such step of folding such at least one first elongated strap portion around the at least one first longitudinal element comprises the step looping such at least one first elongated strap portion clockwise around the at least one first longitudinal element; and such step of folding such at least one second elongated strap portion around the at least one second longitudinal element comprises the step of looping such at least one second elongated strap portion counter-clockwise around the at least one second longitudinal element.

In accordance with another preferred embodiment hereof, this invention provides a method of using a fastening strap system utilized to secure at least one first longitudinal element and at least one second longitudinal element, comprising the steps of: providing at least one a fastening strap system comprising at least one first elongated strap portion comprising, at least one first strap end portion, and at least one first strap width; and at least one second elongated strap portion comprising, at least one second strap end portion, and at least one second strap width; wherein such fastening strap system consists essentially of a unitary portion of flexible sheet material; wherein such unitary portion of flexible sheet material comprises, at least one first side comprising at least one first fastening surface, and at least one second side comprising at least one second fastening surface adapted to be detachably fastenable to such at least one first fastening surface; wherein such second elongated strap portion is offset parallel from such first elongated strap portion a distance about equal to such at least one first strap width; wherein all such at least one first elongated strap portions and all such at least one second elongated strap portions are parallel; creating at least one first loop around the at least one first longitudinal element comprising folding, in a clockwise direction, such at least one first elongated strap portion around the at least one first longitudinal element; and cinching such at least one first elongated strap portion; and creating at least one second loop around the at least one second longitudinal element, wherein such at least one second loop is offset from such at least one first loop by a distance about equal to such at least one first strap width, comprising folding, in a counterclockwise direction, such at least one second elongated strap portion around the at least one second longitudinal element; and cinching such at least one second elongated strap portion.

In accordance with a preferred embodiment hereof, this invention provides a fastening strap system, for selectively removably binding together at least two sets, each such set containing at least one substantially elongated item, comprising: at least two fastening strap elements attached together, each such fastening strap element comprising at least one first side, at least one second side, and at least one strap end portion; and at least one cincher structured and arranged to permit cinching of at least one of such at least two attached fastening strap elements; wherein such at least one cincher comprises at least one aperture; wherein at least one of such at least two attached fastening strap elements is passable at least once through such at least one aperture; wherein at least one first and at least one second respective such fastening strap elements each respectively comprise at least one first surface portion of such at least first side of such at least one strap end portion, and at least one second surface portion of at least one such second side; wherein such at least one first surface portion of such at least one first respective fastening strap element and such at least one second surface portion of such at least one first respective fastening strap element are structured and arranged to promote binding between such at least one first surface portion of such at least one first respective fastening strap element and such at least one second surface portion of such at least one first respective fastening strap element when such at least one first surface portion of such at least one first respective fastening strap element comes in contact with such at least one second surface portion of such at least one first respective fastening strap element; wherein such at least one first surface portion of such at least one second respective fastening strap element and such at least one second surface portion of such at least one second respective fastening strap element are structured and arranged to promote binding between such at least one first surface portion of such at least one second respective fastening strap element and such at least one second surface portion of such at least one second respective fastening strap element when such at least one first surface portion of such at least one second respective fastening strap element comes in contact with such at least one second surface portion of such at least one second respective fastening strap element; wherein each such respective one of such at least two fastening strap elements is structured and arranged to removably loopably bind at least one such set; and wherein such fastening strap system is structured and arranged to permit at least each such respective one of such at least two fastening strap elements, when loopably binding such at least one set, to close with such at least one strap end portion of such each respective one of such at least two fastening strap elements in an exterior position relative to each such respective one of such at least two fastening strap elements.

Moreover, it provides such a fastening strap system wherein such fastening strap system is structured and arranged to permit each such respective one of such at least two fastening strap element to removably loopably bind such at least one set as an operation independent from a similar operation of each other such respective one of such at least two fastening strap elements. Additionally, it provides such a fastening strap system wherein a circumference of such at least one aperture comprises at least one straight transverse edge. Also, it provides such a fastening strap system wherein such at least two attached fastening strap elements and such at least one aperture comprise one integral piece of fastener material. In addition, it provides such a fastening strap system wherein such at least one aperture comprises at least one buckle mechanically attached to at least two of such at least two fastening strap elements.

And, it provides such a fastening strap system wherein at least one of such at least two attached fastening strap elements is at most ninety percent the width of at least one other of such at least two attached fastening strap elements. Further, it provides such a fastening strap system wherein at least one of such at least two attached fastening strap elements is at most half the length of at least one other of such at least two attached fastening strap elements.

Even further, it provides such a fastening strap system wherein such at least two attached fastening strap elements comprise one integral piece of fastener material. Moreover, it provides such a fastening strap system wherein at least one of such at least two fastening strap elements comprises at least one label. Additionally, it provides such a fastening strap system wherein such at least one label is comprises a hook-and-loop material upon which indicia can be written.

In addition, it provides such a fastening strap system wherein such at least one of such at least two fastening strap elements is primarily white. In addition, it provides such a fastening strap system wherein such fastener strap is primarily off-white.

In accordance with another preferred embodiment hereof, this invention provides a continuous-strap system, for allowing a user to create at least one custom-sized fastening strap system for selectively removably binding together at least two sets, each such set containing at least one substantially elongated item, comprising: at least one continuous length of material structured and arranged to permit the user to cut off at least one user-selected portion of such at least one continuous length of material, wherein such at least one continuous length of material is structured and arranged so that the user may select to cut and separate at least two adjacent portions, wherein each of such two adjacent portions comprises at least two attached fastening strap elements, each such fastening strap element comprising at least one first side, at least one second side, and at least one strap end portion; wherein at least one first and at least one second respective such fastening strap elements each respectively comprise at least one first surface portion of such at least first side of such at least one strap end portion, and at least one second surface portion of at least one such second side; wherein such at least one first surface portion of such at least one first respective fastening strap element and such at least one second surface portion of such at least one first respective fastening strap element are structured and arranged to promote binding between such at least one first surface portion of such at least one first respective fastening strap element and such at least one second surface portion of such at least one first respective fastening strap element when such at least one first surface portion of such at least one first respective fastening strap element comes in contact with such at least one second surface portion of such at least one first respective fastening strap element; wherein such at least one first surface portion of such at least one second respective fastening strap element and such at least one second surface portion of such at least one second respective fastening strap element are structured and arranged to promote binding between such at least one first surface portion of such at least one second respective fastening strap element and such at least one second surface portion of such at least one second respective fastening strap element when such at least one first surface portion of such at least one second respective fastening strap element comes in contact with such at least one second surface portion of such at least one second respective fastening strap element; and wherein each such respective one of such at least two fastening strap elements is structured and arranged to removably loopably bind at least one such set.

And, it provides such a continuous-strap system wherein such fastening strap system is structured and arranged to permit at least each such respective at least one fastening strap element, when loopably binding such at least one object, to close with such at least one strap end portion of such each respective at least one fastening strap element in an exterior position relative to such respective at least one fastening strap element.

Further, it provides such a continuous-strap system wherein such continuous length of material comprises at least one aperture. Even further, it provides a continuous-strap system wherein such continuous length of material alternates between wider and thinner widths at regular intervals. Even further, it provides such a continuous-strap system wherein each alternating such wider width has a substantially longer length than each alternating such thinner width. Even further, it provides such a continuous-strap system wherein such continuous length of material comprises at least one aperture adjacent at least one end portion of each such alternating wider width.

In accordance with another preferred embodiment hereof, this invention provides a fastening strap system, for selectively removably binding together at least two sets, each such set containing at least one substantially elongated item, comprising: at least three fastening strap elements attached together, each such fastening strap element comprising at least one first side, at least one second side, and at least one strap end portion; wherein each of such at least three attached fastening strap elements respectively comprises at least one first surface portion of such at least first side of such at least one strap end portion, and at least one second surface portion of at least one such second side; wherein such at least one first surface portion of each such respective one of such at least three attached fastening strap elements and such at least one second surface portion of each such respective one of such at least three attached fastening strap elements are structured and arranged to promote binding between such at least one first surface portion of each such respective one of such at least three attached fastening strap elements and such at least one second surface portion of each such respective one of such at least three attached fastening strap elements when such at least one first surface portion of each such respective one of such at least three attached fastening strap elements comes in contact with such at least one second surface portion of each such respective one of such at least three attached fastening strap elements; wherein each such respective one of such at least three attached fastening strap elements is structured and arranged to removably loopably bind at least one such set; and wherein such fastening strap system is structured and arranged to permit at least each such respective one of such at least three attached fastening strap elements, when loopably binding such at least one set, to close with such at least one strap end portion of such each respective one of such at least three attached fastening strap elements in an exterior position relative to each such respective one of such at least three attached fastening strap elements.

Even further, it provides such a fastening strap system wherein such at least three attached fastening strap elements comprise at least four attached fastening strap elements.

In accordance with another preferred embodiment hereof, this invention provides a fastening strap system, for selectively removably binding together at least two sets, each such set containing at least one substantially elongated item, comprising: at least two fastening strap elements attached together, each such fastening strap element comprising at least one first side, at least one second side, and at least one strap end portion; wherein at least one first and at least one second respective such fastening strap elements each respectively comprise at least one first surface portion of such at least first side of such at least one strap end portion, and at least one second surface portion of at least one such second side; wherein such at least one first surface portion of such at least one first respective fastening strap element and such at least one second surface portion of such at least one first respective fastening strap element are structured and arranged to promote binding between such at least one first surface portion of such at least one first respective fastening strap element and such at least one second surface portion of such at least one first respective fastening strap element when such at least one first surface portion of such at least one first respective fastening strap element comes in contact with such at least one second surface portion of such at least one first respective fastening strap element; wherein such at least one first surface portion of such at least one second respective fastening strap element and such at least one second surface portion of such at least one second respective fastening strap element are structured and arranged to promote binding between such at least one first surface portion of such at least one second respective fastening strap element and such at least one second surface portion of such at least one second respective fastening strap element when such at least one first surface portion of such at least one second respective fastening strap element comes in contact with such at least one second surface portion of such at least one second respective fastening strap element; wherein each such respective one of such at least two fastening strap elements is structured and arranged to removably loopably bind at least one such set; and wherein at least one of such at least two fastening strap elements comprises at least one label.

Even further, it provides such a fastening strap system wherein such at least one label comprises a hook-and-loop material upon which indicia can be written. Even further, it provides such a fastening strap system wherein at least one of such at least two fastening strap elements is primarily white. Even further, it provides such a fastening strap system wherein at least one of such at least two fastening strap elements is primarily off-white.

Even further, it provides such a fastening strap system wherein such fastening strap system is structured and arranged to permit at least each such respective one of such at least two fastening strap elements, when loopably binding such at least one set, to close with such at least one strap end portion of such each respective one of such at least two fastening strap elements in an exterior position relative to each such respective one of such at least two fastening strap elements.

In accordance with a preferred embodiment hereof, this invention provides a fastening strap system relating to securing at least two elements to be secured, comprising: at least one first elongated strap portion each comprising, at least one first strap end portion, at least one first strap width, and at least one first strap length; at least one second elongated strap portion each comprising, at least one second strap end portion, at least one second strap width, and at least one second strap length; at least one aperture comprising, at least one aperture width, and at least one aperture length; wherein such fastening strap system consists essentially of a unitary portion of flexible sheet material; wherein such unitary portion of flexible sheet material comprises, a first side having its entire first-side surface substantially comprising at least one first fastening surface, and a second side having its entire second-side surface substantially comprising at least one second fastening surface adapted to be detachably fastenable to such at least one first fastening surface; wherein all such at least one first elongated strap portions and all such at least one second elongated strap portions are parallel and collinear; wherein such at least one aperture is located between such at least one first strap end portion of such at least one first elongated strap portion and such at least one second strap end portion of such at least one second elongated strap portion; and wherein such at least one aperture width is sized so as to be able to receive such at least one first elongated strap portion without requiring twisting along at least one longitudinal axis of such at least one first strap length of such at least one first elongated strap portion; wherein such second strap width, without bending or folding along such at least one second strap length of such at least one second elongated strap portion, prevents insertion of such at least one second elongated strap portion into such at least one aperture; wherein such at least one first fastening surface comprises at least one hook fastening surface; wherein such at least one second fastening surface comprises at least one complementary fastening surface; wherein such fastening system is structured and arranged to form at least one first fastening loop, such first fastening loop formed by encirclement of such at least one first elongated strap portion around at least one first element to be secured, insertion of at least such first strap end portion of such at least one first elongated strap portion into and through such at least one aperture, and cinching of such at least one first elongated strap portion to secure the at least one first element to be secured, wherein such at least one first fastening loop is secured by connection of such at least one first fastening surface and such at least one second fastening surface, wherein such fastening is finely adjustable; and wherein such fastening system is further structured and arranged to form at least one second fastening loop formed by encirclement of such at least one second elongated strap portion around at least one second element to be secured wherein such at least one second fastening loop is secured by connection of such at least one first fastening surface and such at least one second fastening surface, wherein such fastening is finely adjustable. Moreover, it provides such a strap system wherein such at least one first strap length is different than such at least one second strap length. Additionally, it provides such a strap system wherein such at least one aperture comprises a portion devoid of such flexible sheet material. Also, it provides such a strap system wherein such at least one first strap width is not substantially greater than such at least one aperture width. In addition, it provides such a strap system wherein: such at least one first strap width is less than such at least one second strap width; such at least one aperture width is less than such at least one second strap width; and wherein such at least one second elongated strap portion contains such at least one aperture. And, it provides such a strap system wherein such at least one first elongated strap portion comprises at least one label. Further, it provides such a strap system wherein such at least one second elongated strap portion comprises at least one label. Even further, it provides such a strap system wherein such first side is different in color than such second side. Moreover, it provides such a system wherein such at least one aperture comprises at least one transverse slit. Additionally, it provides such a strap system comprising at least two of such at least one aperture. Also, it provides such a system wherein such at least one second fastening surface comprises at least one complementary hook fastening surface. In addition, it provides such a system wherein such at least one second fastening surface comprises at least one loop fastening surface. And, it provides such a strap system wherein such second side is lighter in color than such first side. Further, it provides such a strap system wherein such second side comprises such at least one loop fastening surface and such at least one second side is lighter in color than such first side. Even further, it provides such a strap system wherein such at least one second strap width is the widest portion of such fastening strap system.

In accordance with another preferred embodiment hereof, this invention provides a fastening strap system, comprising: at least one first elongated strap portion comprising, at least one first strap end portion, at least one first strap width, and at least one first strap length; at least one second elongated strap portion comprising, at least one second strap end portion, and at least one second strap width; and at least one aperture comprising, at least one aperture width, and at least one aperture length; wherein such fastening strap system consists essentially of a unitary portion of flexible sheet material; wherein such unitary portion of flexible sheet material comprises, at least one first side having its entire first-side surface substantially comprising at least one first fastening surface, and at least one second side having its entire second-side surface substantially comprising at least one second fastening surface adapted to be detachably fastenable to such at least one first fastening surface; wherein all such at least one first elongated strap portions and all such at least one second elongated strap portions are parallel and collinear; wherein such at least one aperture is located between such at least one first strap end portion and such at least one second strap end portion; wherein such at least one aperture is structured and arranged to allow cinching such at least one first elongated strap portion around at least one first element to be secured by insertion of such at least one first elongated strap portion into and through such at least one aperture, thereby forming at least one first fastening loop, such at least one first fastening loop fastened by connection of such at least one first fastening surface with such at least one second fastening surface; wherein, when cinching, such at least one first elongated strap portion is finely adjustable about such at least one first strap length; wherein such at least one first strap width is less than such at least one second strap width; wherein such at least one second strap width, without bending or folding along such at least one second strap length of such at least one second elongated strap portion, prevents insertion of such at least one second elongated strap portion into such at least one aperture; wherein such at least one elongated strap portion contains such at least one aperture; wherein such at least one second strap width is the widest portion of such fastening strap system; and wherein such at least one first strap end portion is shorter than such at least one second strap end portion; and wherein such at least one second elongated strap portion is structured and arranged to be cinched around at least one second element to be secured by encircling such at least one second elongated strap portion around the at least one second element to be secured, thereby forming at least one second fastening loop, such at least one second fastening loop fastened by connection of such at least one first fastening surface with such at least one second fastening surface, wherein such fastening is finely adjustable.

BRIEF DESCRIPTION OF THE DRAWINGS

FIG. 1 shows a prior art strap wrapped around a bundle.

FIG. 2 shows a sheet of prior art strap material apportioned for die cut manufacturing.

FIG. 3 shows a plan view of an offset-relationship two-ended strap in an embodiment of the present invention, showing a single strap cut from a sheet of material used in embodiments of the present invention.

FIG. 4 shows a perspective view of the offset-relationship two-ended strap of FIG. 3, shown bundling two separate sets of items together in an embodiment of the present invention.

FIG. 5 shows another perspective view of the offset-relationship two-ended strap of FIG. 3 and FIG. 4.

FIG. 6 shows a plan view of an embodiment of the present invention, a parallel-relationship two-ended strap.

FIG. 7 shows a side view of the parallel-relationship two-ended strap of FIG. 6 with the two straps formed into loops.

FIG. 8 shows a perspective view of the parallel-relationship two-ended strap of FIGS. 6 and 7 in an embodiment of the present invention.

FIG. 9 shows a perspective view of the parallel-relationship two-ended strap of FIGS. 6-8, shown in use around two separate cylindrical items in an embodiment of the present invention.

FIG. 10 shows a plan view of an embodiment of the present invention, a parallel-relationship four-ended strap.

FIG. 11 shows a side view of the opposed-parallel-relationship four-ended strap of FIG. 10 with the four straps formed into loops.

FIG. 12 shows a plan view of an embodiment of the present invention, a parallel-relationship three-ended strap.

FIG. 13 shows a side view of the parallel-relationship three-ended strap of FIG. 12 with the three straps formed into loops surrounding three cylindrical tubular objects.

FIG. 14 shows a plan view of an embodiment of the present invention, a Y-configuration three-ended strap.

FIG. 15 shows a side view of the Y-configuration three-ended strap of FIG. 14 with the three straps formed into different size loops.

FIG. 16 shows a plan view of an embodiment of the present invention, an open-center-configuration two-ended strap.

FIG. 17 shows a side view of the open-center-configuration two-ended strap of FIG. 16 shown with two loops formed with the ends passing through the open-center.

FIG. 18 shows a plan view of another embodiment of the offset-relationship two-ended strap.

FIG. 20 shows a close-up edge view of a hook and loop material as used in embodiments of the present invention.

FIG. 21 shows a close-up edge view of a hook and hook material as used in embodiments of the present invention.

FIG. 22 shows a plan view, showing both front and rear surfaces, of an alternating hook/loop material used in embodiments of the present invention.

FIG. 23 shows a plan view of an alternative embodiment of the present invention, an open-center-configuration two-ended strap.

FIG. 24 shows a side partial view of an alternative embodiment of the present invention, an open-center-configuration two-ended strap.

FIG. 25 shows a perspective view of an alternative embodiment of the present invention, a two-ended strap with a thinner shorter end and a wider longer end with a label.

FIG. 26 shows a perspective view of the fastener strap system of FIG. 25, anchored to an object with the small strap.

FIG. 27 shows a perspective view of the fastener strap system of FIG. 25, anchored to an object with the small strap and binding a second object with the larger strap.

FIG. 28 shows a perspective view of an alternative embodiment of the present invention, a reel of a continuous length of strap material with at least one aperture.

FIG. 33 shows a plan view of a two-ended fastening strap, according to a preferred embodiment of the present invention.

FIG. 34 shows a reel of continuous material having separable portions, according to a preferred embodiment of the present invention.

FIG. 35 shows a plan view of a portion of the reel of FIG. 34.

FIG. 36 shows a perspective view of the two-ended fastening strap of FIG. 33.

FIG. 37 shows a plan view of a fastening strap, according to another preferred embodiment of the present invention.

FIG. 38 shows a reel of continuous material having separable portions, according to another preferred embodiment of the present invention.

FIG. 39 shows a plan view of a portion of the reel of FIG. 38.

FIG. 40 shows a perspective view of the fastening strap of FIG. 37.

DETAILED DESCRIPTION OF PREFERRED EMBODIMENTS AND THE BEST MODES OF PRACTICE

Figure 29:
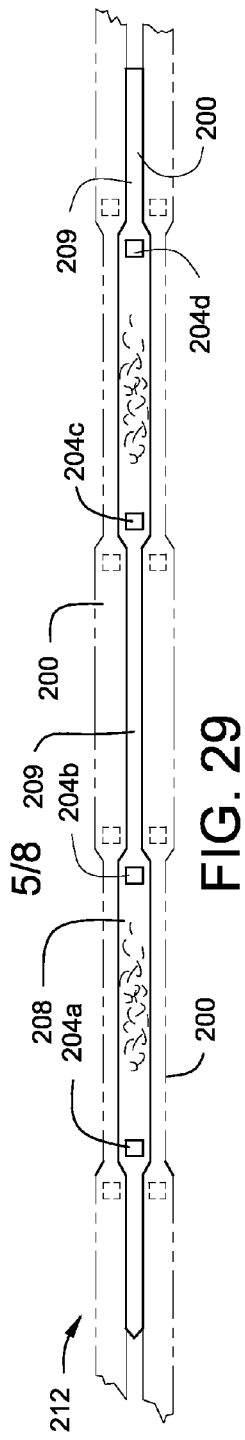
FIG. 29 shows a plan view of a portion of the continuous length of strap material shown in FIG. 28, along with indications of a method of efficiently manufacturing such from a sheet of material.

Preferred embodiments and best mode of the present invention are described below. In such discussion, reference will be made to hook and loop fasteners. It is noted that the present invention, in a described embodiment, provides a simple dispensing mechanism for dispensing straps of variable length determined by the end user, having been preferably provided the material, preferably pre-cut by a manufacturer (to provide such advantages).

FIG. 20 shows a close-up edge view of a hook and loop material 160 as used in embodiments of the present invention. Preferably, the hook and loop material 160 comprises loop material 162 and hook material 164. Preferably, hook and loop material may also be made, according to the present invention, as illustrated in FIG. 22.

FIG. 22 shows a plan view, showing both front and rear surfaces, of an alternating hook/loop material used in some embodiments of the present invention. Preferably, the hook and loop material 170 comprises, on a first side 171, diagonal bands of hook material 172 alternating with diagonal bands of loop material 174 (embodying herein, wherein said at least one first surface portion of said at least one first respective fastening strap element and said at least one second surface portion of said at least one first respective fastening strap element are structured and arranged to promote binding between said at least one first surface portion of said at least one first respective fastening strap element and said at least one second surface portion of said at least one first respective fastening strap element when said at least one first surface portion of said at least one first respective fastening strap element comes in contact with said at least one second surface portion of said at least one first respective fastening strap element). Preferably, the hook and loop material 170 further comprises, on a second side 173, diagonal bands of hook material 176 alternating with diagonal bands of loop material 178. Preferably, as shown, the relationship between the diagonal bands on the opposing sides 171 and 173 is such that the diagonal rows are substantially perpendicular to each other.

Preferably, a third material comprises a hook and hook material as shown in FIG. 21. FIG. 21 shows a close-up edge view of a hook and hook material 168 as used in embodiments of the present invention. The hook and hook material 168 comprises rows of hooks 166 on one or, as shown, both sides of hook and hook material 168. Each hook on hook and hook material 168 preferably comprises at least one mushroom-shaped head, preferably at least one three-dimensional mushroom shaped head. Upon reading the teachings of this specification, those skilled in the art will now appreciate that, under appropriate circumstances, considering such issues as available materials, cost, future technologies, etc., other hook and hook materials, such as, for example, single hook to multiple hooks fastening materials, lop-sided mushroom-shaped hook and hook materials, multi-directional barb hook materials, etc., may suffice. Under appropriate circumstances, the hook and hook material may be preferable for the below described embodiments of the present invention. Those skilled in the art will appreciate the features of all three of the above described fastener materials and the desirability of their usage under appropriate circumstances. Thus, although the below discussion makes reference to hook and loop materials or fasteners, such usage is defined to comprise, under appropriate circumstances, any of the above three described fasteners.

Hook and loop material 160, hook and loop material 170, and hook and hook material 168 preferably comprise at least one durable material, preferably at least polyester and nylon. Alternately, hook and loop material 160, hook and loop material 170, and hook and hook material 168 preferably comprise at least one medical grade material, preferably at least one bio-absorbable material, preferably at least polyester (PET) and polylactic acid (PLA). Upon reading the teachings of this specification, those skilled in the art will now appreciate that, under appropriate circumstances, considering such issues as available materials, cost, future technologies, etc., other materials, such as, for example, other durable materials, other bio-absorbable materials, etc., may suffice.

FIG. 3 shows a plan view of an offset-relationship two-ended strap 124 (embodying herein a fastening strap system), according to a preferred embodiment of the present invention, which illustrates the offset-relationship two-ended strap 124 shown as having been cut from a single sheet 122 of material used in embodiments of the present invention, wherein the layout of the offset-relationship two-ended straps 124 upon the sheet 122 allows an efficient manufacture of at least one offset-relationship two-ended strap 124. Preferably, as shown, the configuration of the straps is such that successive offset-relationship two-ended straps 124 result from the placement and removal of adjacent offset-relationship two-ended straps 124. Thus, those of ordinary skill in the art will now appreciate that, under appropriate circumstances, considering issues such as ease in bundling, preventing unbundling, object accessibility, etc., other arrangements, such as each of the subsequent embodiments of the fastening straps further described below, not limited to FIG. 3, may be preferred. Preferably, each offset-relationship two-ended strap 124 comprises an end 124a (embodying herein at least one first fastening strap element comprising at least one first side, at least one second side, and at least one strap end portion wherein such at least one first fastening strap element comprises at least one first surface portion of such at least one first side of such at least one strap end portion, and at least one second surface portion of at least one such second side) and an end 124b (embodying herein at least one second fastening strap element comprising at least one first side, at least one second side, and at least one strap end portion wherein such at least one first fastening strap element comprises at least one first surface portion of such at least one first side of such at least one strap end portion, and at least one second surface portion of at least one such second side), each with first side 300 and second side 302, having a parallel, offset, configuration.

Figure 31:
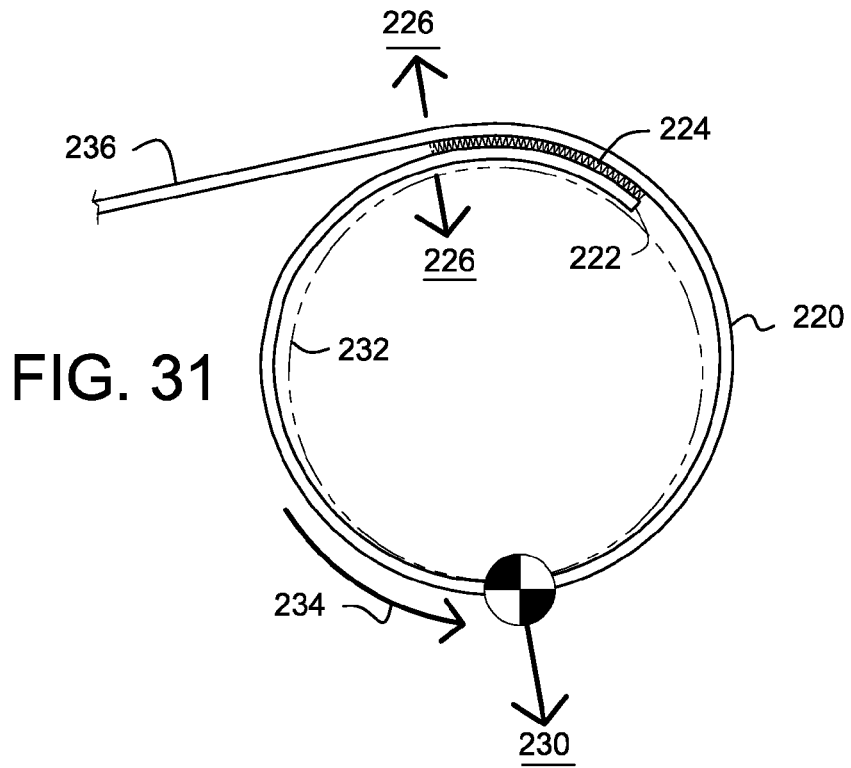
FIG. 31 shows a loop binding arrangement.
Figure 32:
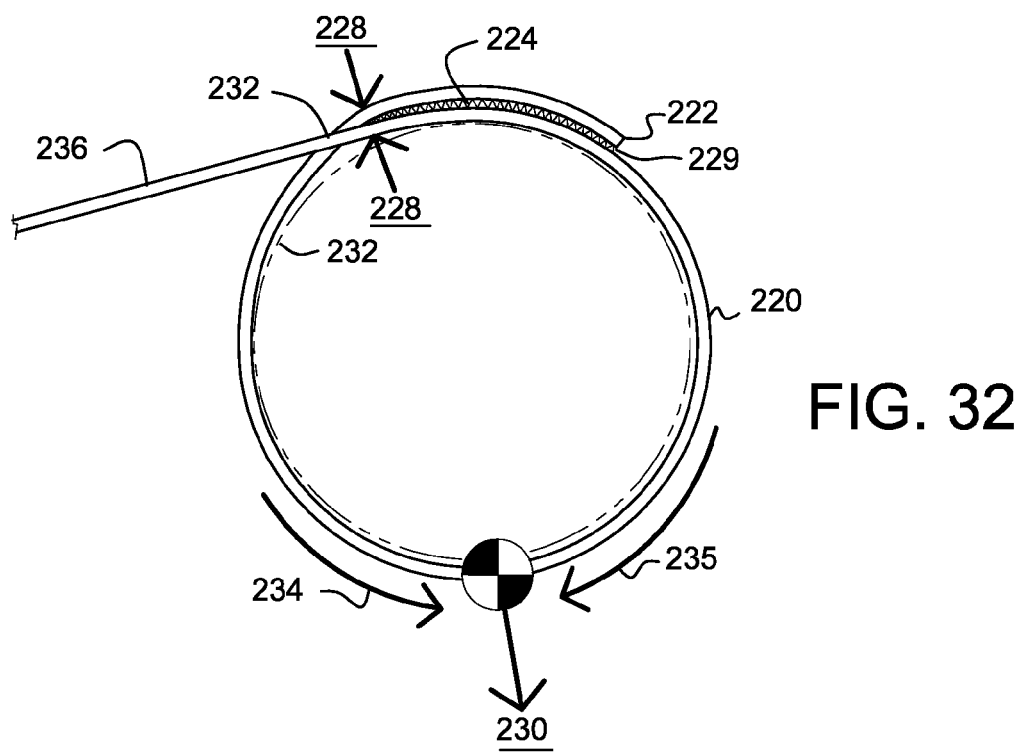
FIG. 32 shows a preferred loop binding arrangement.

It is very especially noted that, when using fasteners comprising VELCRO-type material to form a loopable binding, the position of the strap end 222 plays an important role in the strength of the binding, and the likelihood of the binding unintentionally coming undone. When the strap end 222 is fastened inside the loop of the binding, as in FIG. 31, it is much more likely to unintentionally come undone, because a force 230 (such as gravity, etc.) working on the bound object will tend to pull apart the leading edge 226 of the bond 224 between the restrained portion 236 and the strap end 222. Such a force will tend to "unravel" the loop binding. Similarly an angular twisting force 234 will have a similar unraveling effect. Preferably, as shown in FIG. 32, an offset (or an aperture through the strap) allows strap end 222 to pass by (or through) the restrained portion 236 near location 231, permitting the loop binding to be closed with the strap end in the exterior position. When the strap end 222 is fastened to the outside of the loop, as shown in FIG. 32, the binding is much less likely to unintentionally come undone, because a force 230 working on the bound object will tend to press the strap end 222 against the restrained portion 236 of the fastening strap element 220, strengthening the leading edge 228 of the bond 224. Preferably, the restrained portion 236 is restrained by the other object(s) to which the fastening strap system is attached. Preferably, as shown in FIG. 32, a twisting force 235 does not unravel the trailing end 229 of the bond 224 since the termination of the strap end 222 is not restrained. It is therefore preferable for a loop binding to be arranged, as shown in FIG. 32, with the strap end 222 in an exterior position (embodying herein wherein said fastening strap system is structured and arranged to permit at least each said respective at least one fastening strap element, when loopably binding such at least one object, to close with said at least one strap end portion of said each respective at least one fastening strap element in an exterior position relative to said respective at least one fastening strap element).

Preferably, loop bindings close by forming a bond between first side 300 and second side 302, as shown in FIG. 32 (embodying herein, wherein each said respective at least one fastening strap element is structured and arranged to removably loopably bind at least one such object). "Folding" first side 300 back upon another portion of first side 300 (even if the materials provide for such a bond) would result in an arrangement less preferable, since a force 230 acting on an enclosed object would work to pull apart the leading edge 226 of the bond 224.

Preferably, the offset, or a passage through an aperture of the strap (as seen in later embodiments), allows each strap to operate independently from the other, and permits each strap to fasten with the strap end in an exterior position (examples are shown in FIG. 5, FIG. 8, and FIG. 17). Without the offset (or passage), the two (or more) straps interfere with each other, preventing independent operation and proper closure with the strap end in an exterior position.

Referring to FIG. 4, a perspective view of the offset-relationship two-ended strap 124 of FIG. 3, such strap is shown bundling two separate sets of items together according to a preferred embodiment of the present invention. As shown, the offset relationship provides the feature of allowing the secure bundling of a first set 126 by end 124b while also allowing the independent secure bundling of a second set 128 by end 124a.

Referring to FIG. 5, another perspective view of the offset-relationship two-ended strap of FIG. 3 and FIG. 4 is shown. The particular arrangement of the offset-relationship two-ended strap 124 has a feature of being particularly well suited for the bundling of objects where the wrapping motion used to place the two ends 124a and 124b around the objects being bundled is best done using opposite direction, or rotation wrapping movements, of the strap ends 124a and 124b. As further shown, two-ended strap 124 comprises two surfaces, a hook surface 127 and a loop surface 125. Preferably, as shown, each end 124a and 124b will fasten upon itself when looped back such that either of the two surfaces, the hook surface 127 and the loop surface 125, is placed over and then upon the other surface FIG. 6 shows a plan view of a parallel-relationship two-ended strap, according to a preferred embodiment of the present invention. Preferably, the parallel-relationship two-ended strap 130 possesses similar manufacturing features as previously mentioned. Preferably, the parallel-relationship two-ended strap 130 comprises two parallel ends 130a and 130b.

Two-ended strap 130 and two-ended strap 124 preferably comprise at least one durable material, preferably at least polyester and nylon. Alternately, two-ended strap 130 and two-ended strap 124 preferably comprise at least one medical grade material, preferably at least one bio-absorbable material, preferably at least polyester (PET) and polylactic acid (PLA). Upon reading the teachings of this specification, those skilled in the art will now appreciate that, under appropriate circumstances, considering such issues as available materials, cost, future technologies, etc., other materials, such as, for example, other durable materials, other bio-absorbable materials, etc., may suffice.

Referring to FIG. 7, a side view of the parallel-relationship two-ended strap 130 of FIG. 6 with the two strap ends 130a and 130b formed into loops is shown; and referring to FIG. 8, a perspective view of the parallel-relationship two-ended strap 130 of FIGS. 6 and 7 are shown. Preferably, the parallel-relationship two-ended strap 130 comprises two substantially similar ends 130a and 130b that may be looped back upon themselves to form two binding loops, as shown. Preferably, as previously discussed in reference to FIGS. 3-5, the front and back surfaces of the parallel-relationship two-ended strap 130 comprise hook and loop fastener components. It can be seen that the design of the parallel-relationship two-ended strap 130 provides a feature of a different wrapping action of the two ends 130a and 130b than that previously discussed in reference to FIGS. 3 and 4. Upon reading this specification, those of ordinary skill in the art will now recognize that, under appropriate circumstances, considering issues such as cost, flexibility, ease in bundling, preventing unbundling, object accessibility, etc., other arrangements, such as the offset-relationship two-ended strap 124, non-two-ended straps, etc., may be preferred.

Referring to FIG. 9, the parallel-relationship two-ended strap 130 is shown with the end 130a wrapped around an object 132 and the end 130b wrapped around an object 134.

FIG. 10 shows a plan view of an opposed-parallel-relationship four-ended strap, according to a preferred embodiment of the present invention. Preferably, the opposed-parallel-relationship four-ended strap 140 comprises four ends 140a-d, in two parallel and opposing sets (embodying herein, wherein said at least one attached fastening strap elements comprises at least four fastening strap elements). Preferably, the opposed-parallel-relationship four-ended strap 140 comprises hook and loop surfaces in the manner already discussed.

FIG. 11 shows a side view of the opposed-parallel-relationship four-ended strap 140 of FIG. 10 with the four strap ends 140a through 140d formed into loops. Those skilled in the art will recognize that, in appropriate circumstances, the opposed-parallel-relationship four-ended strap 140 features, in terms of flexibility of bundling, may be more favorable than those of the previous fastening straps.

Referring to FIG. 12, a plan view of another preferred embodiment of the present invention, a parallel-relationship three-ended strap is shown. Preferably, the parallel-relationship three-ended strap 144 comprises three parallel ends 144a, 144b, and 144c (embodying herein, wherein said at least one attached fastening strap elements comprises at least three fastening strap elements). Preferably, the parallel-relationship three-ended strap 144 possesses similar manufacturing features as previously mentioned. The parallel-relationship three-ended strap 144 comprises three substantially similar ends 144a, 144b, and 144c that may be looped back upon themselves to form three binding loops. Preferably, as previously discussed, the front and back surfaces of the parallel-relationship three-ended strap 144 comprise hook and loop fastener components. Upon reading this specification, those of ordinary skill in the art will now recognize that, under appropriate circumstances, considering issues such as flexibility, ease in bundling, preventing unbundling, object accessibility, cost, etc., other arrangements, such as the use of a fastener with more than three ends, such as any other non-three-ended strap, etc., may suffice.

FIG. 13 shows a side view of the parallel-relationship three-ended strap 144 of FIG. 12, with the three strap ends 144a, 144b, and 144c formed into loops surrounding three cylindrical tubular objects 146a, 146b, and 146c, respectively. As discussed in regard to the previous embodiments, a feature of embodiments of the present invention is the ability to provide for the selective and independent binding and release of multiple bundles of items from one another. Preferably, the parallel-relationship three-ended strap 144 is such a fastening strap (i.e., one that permits either a fastened set A and/or set B to be further fastened to yet a third set C without alteration of the remaining fastened sets). For example, with a set A ski poles and a set B skis, one might decide to keep either the ski poles or the skis bundled and then attach that remaining bundled set to a third set C such as a car roof rack. Preferably, the parallel-relationship three-ended strap 144 provides the feature of allowing the fastening of both a set A and a set B, but then further allows the release of either set A or set B while leaving the remaining set fastened intact, which set could then in turn be immediately attachable to a third set C.

Referring to FIG. 14, a plan view of another preferred embodiment of the present invention, a Y-configuration three-ended strap is shown. The Y-configuration three-ended strap 148 comprises three ends 148a, 148b, and 148c configured into a Y pattern as shown. The three ends 148a, 148b, and 148c of the Y-configuration three-ended strap 148 may be looped back upon themselves to form three binding loops (as in FIG. 15). As previously discussed, the front and back surfaces of the parallel-relationship three-ended strap 148 comprise hook and loop fastener components. Those skilled in the art will now recognize that, in appropriate circumstances, the availability of three ends 148a, 148b, and 148c, in a Y configuration, is a feature that may be preferred.

FIG. 15 shows a side view of the Y-configuration three-ended strap 148 of FIG. 14, with the three strap ends 148a, 148b, and 148c formed into three different size loops. The independent and selectable formation of three fastening loops of adjustable sizing is a feature of this embodiment of the present invention, the Y-configuration three-ended strap 148.

Four-ended strap 140, three-ended strap 144 and Y-configuration three-ended strap 148 preferably comprise at least one durable material, preferably at least polyester and nylon. Alternately, four-ended strap 140, three-ended strap 144 and Y-configuration three-ended strap 148 preferably comprise at least one medical grade material, preferably at least one bio-absorbable material, preferably at least polyester (PET) and polylactic acid (PLA). Upon reading the teachings of this specification, those skilled in the art will now appreciate that, under appropriate circumstances, considering such issues as available materials, cost, future technologies, etc., other materials, such as, for example, other durable materials, other bio-absorbable materials, etc., may suffice.

Referring to FIG. 16, a plan view is shown of a highly preferred embodiment of the present invention, an open-center-configuration two-ended strap. Preferably, the open-center-configuration two-ended strap 150 comprises substantially straight transverse edge, preferably substantially rectangular, preferably substantially square, as shown. Preferably, center portion 154 is structured to be a substantially rectangular, preferably substantially square, center aperture 152 or opening (embodying herein, wherein said at least one cincher comprises at least one aperture; and at least one of said at least one attached fastening strap elements is passable at least once through said at least one aperture). The open-center configuration two-ended strap 150, also comprises two ends 150a and 150b, as shown (the entire end 150a is like end 150b). Preferably, as previously discussed, the front and back surfaces of the open-center-configuration two-ended strap 150 comprise hook and loop fastener components. Preferably, the two ends 150a and 150b are sized in cooperation with the center portion 154, such that the two ends 150a and 150b may be passed through the center portion aperture 152 to form loops. Upon reading this specification, those of ordinary skill in the art will now recognize that, under appropriate circumstances, considering issues such as flexibility, ease in bundling, preventing unbundling, object accessibility, etc., other arrangements, such as passing the two ends 150a and 150b, one or more times, through the aperture 152 of center portion 154, etc., may suffice. Preferably, this embodiment provides a feature of allowing an amount of flexibility between the two loops formed from the ends 150a and 150b while also permitting cinching (embodying herein at least one cincher structured and arranged to permit cinching of at least one of said at least one attached fastening strap elements) and securely binding the objects fastened with the loops formed by the ends 150a and 150b. Preferably, depending on the length of the ends 150a and 150b, they may be looped multiple times through the aperture 152 of center portion 154, thus providing for additional binding strength, as each successive layer of the hook and loop material will successively fasten upon itself, as each loop is wound.

Open-center-configuration two-ended strap 150 preferably comprises at least one durable material, preferably at least polyester and nylon. Alternately, open-center-configuration two-ended strap 150 preferably comprises at least one medical grade material, preferably at least one bio-absorbable material, preferably at least polyester (PET) and polylactic acid (PLA). Upon reading the teachings of this specification, those skilled in the art will now appreciate that, under appropriate circumstances, considering such issues as available materials, cost, future technologies, etc., other materials, such as, for example, other durable materials, other bio-absorbable materials, etc., may suffice.

Figure 19:
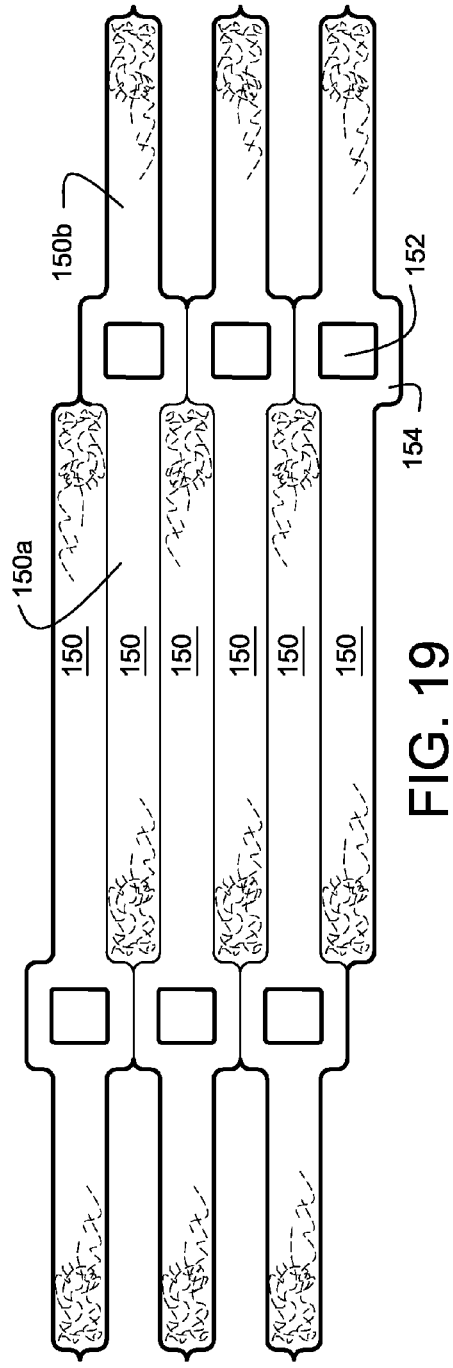
FIG. 19 (on sheet 5) shows a plan view of at least one open-center-configuration two-ended straps showing a preferred material saving economical layout of the open-center-configuration two-ended straps upon a sheet of material used in embodiments of the present invention.

FIG. 19 (on sheet 5) shows a plan view of at least one open-center configuration two-ended strap 150 showing a preferred material-saving economical layout of the open-center configuration two-ended straps 150, upon a sheet of material used in embodiments of the present invention (embodying herein, wherein said at least one attached fastening strap elements comprises one integral piece of fastener material). Preferably, this layout conserves fastener material and minimizes manufacturing costs, as only a single cut is needed between adjacent open-center configuration two-ended straps 150.

Referring to FIGS. 23 and 24, an alternate embodiment of the present invention, an alternative open-center-configuration two-ended strap is shown, respectively, from the top and from the side. Preferably, the alternative open-center-configuration two-ended strap 182 comprises a center buckle 186 to which is coupled to two fastening strap ends 184 and 188 (embodying herein, wherein said at least one aperture comprises at least one buckle mechanically attached to at least two said fastening strap elements). Preferably, the two fastening strap ends 184 and 188 are sized in cooperation with the center buckle 186 such that the two fastening strap ends 184 and 188 may be passed through the center buckle 186 to form loops. Upon reading this specification, those of ordinary skill in the art will now appreciate that, considering issues such as flexibility, ease in bundling, preventing unbundling, object accessibility, etc., other arrangements, such as passing the two fastening strap ends 184 and 188, one or more times, through the center buckle 186, etc., may suffice. For example, this embodiment provides a feature of allowing an amount of flexibility between the two loops formed from the two fastening strap ends 184 and 188 while also securely binding the objects fastened with the loops formed by the two fastening strap ends 184 and 188. The flexibility is due to the length and configuration of the center buckle 186. Preferably, depending on the length of the two fastening strap ends 184 and 188, they may be looped multiple times through the center buckle 186, thus providing for additional binding strength as each successive layer of the hook and loop material will successively fasten upon itself as each loop is wound.

FIG. 25 shows an alternate embodiment of the present invention, an alternative two-ended strap comprising a relatively shorter and narrower anchor strap 200 and a relatively longer wider main strap 202. In this alternate embodiment, aperture 204 is preferably sized to allow anchor strap 200 to pass through aperture 204 at least once. Preferably, anchor strap 200 provides for convenient anchoring of the strap system to an object without the excessive bulk or hassle of threading a larger strap through an aperture. Preferably, anchor strap 200 is at least 90% narrower than the width of main strap 202 (as shown, see FIG. 25). Applicant notes that FIG. 25 clearly shows that the width of aperture 204 is preferably sized so as to be able to receive anchor strap 200 without requiring twisting along the longitudinal axis of anchor strap 200, as shown. Applicant further notes that the width of aperture 204 is preferably sized to prevent insertion of main strap 202 without bending or folding main strap 202 along the length of main strap 202, as shown. Preferably, anchor strap 200 is, at most, half the length of main strap 202. Preferably, anchor strap 200 is bound to one object, while main strap 202 is bound to several objects. Preferably, this strap system provides smaller anchor strap 200, which allows the strap system to be quickly and conveniently anchored without excessive threading. Preferably, this strap system provides a longer-and-wider main strap 202 to bundle numerous and/or larger, bulkier objects. Upon reading this specification, those of ordinary skill in the art will now appreciate that, under appropriate circumstances, considering issues such as flexibility, ease in bundling, preventing unbundling, object accessibility, etc., other arrangements, such as pulling main strap 202 through aperture 204, even if main strap is wider then aperture 204, by folding/bending main strap 202, etc., may suffice. Preferably, main strap 202 also comprises a label 206 (embodying herein, wherein at least one said fastener strap element comprises at least one label). Preferably, main strap 202 (for example) comprises a material that is conducive to being written upon so that the strap system may be labeled by a user. Preferably, a portion of the material comprises a light color, preferably white, preferably off-white, so that there will be contrast (providing better legibility) to the dark ink which is typically used for writing. Preferably, label 206 is located on one side of the strap being written on (e.g., main strap 202). Alternatively, label 206 is preferred to be located on both sides of the strap. Preferably, label 206 is located on a user-selected side of the strap, depending on whether user wants label to show or not, when the strap is being used.

FIG. 27 shows a strap system with a label 206 on the outside being used to loopably bind two objects together. If label 206 were only on the other side of the strap, the label could remain concealed until the main strap 202 is unbound, which may be desirable for certain applications, such as for aesthetic reasons.

Figure 30:
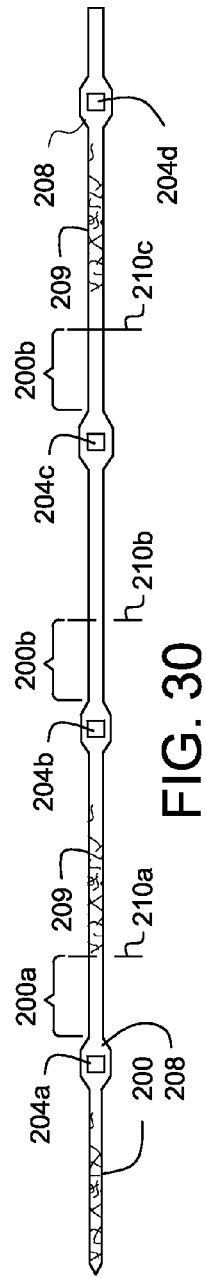
FIG. 30 shows a plan view of a portion of an alternative embodiment of the present invention, an alternative continuous length of strap material with at least one apertures.

FIG. 28 shows a perspective view of a reel 205 of continuous strap material, with at least one aperture 204 which can be cut to a length desired by a user (embodying herein a continuous-strap system). FIG. 29 and FIG. 30 show, in plan view, portions of two alternate preferred embodiments of such continuous strap material. Preferably, the reel 205 of continuous strap material provides the user with flexibility by allowing a user to select the optimal length of the straps for each particular application. Preferably, the continuous length of strap material 205 alternates between wide cross section 208 and narrow cross section 209 (corresponding to the widths of the anchor strap 200 and the main strap 202 that are formed when the material is cut from reel 205) at regular intervals, as shown. Preferably, apertures 204 are located at regular intervals within the wide cross section 208 of the material, as shown. Preferably, each alternating wide portion is longer (preferably at least twice as long) than each alternating thinner portion. Preferably, a user cuts a length of the continuous strap either somewhere in the middle of one of the thinner sections or at an end of one of the thinner sections, thereby creating an anchor strap 200 on at least one end, which can be used as described above. For example, referring to FIG. 30, a user could cut the material at location 210*a*, 210*b*, or 210*c*, etc., thereby creating anchor strap 200*a*, 200*b*, or 200*c*, etc., respectively, (preferably for use with aperture 204*a*, 204*b*, or 204*c*, respectively). The prior art strap, as shown in FIG. 1 and FIG. 2, only comes in a fixed length, which is unlikely to be the optimal length for any particular application by a user (imagine SCOTCH® brand tape only being available in precut two-inch strips). Preferably, the apertures 204 in the continuous strap 205 of the embodiment of the present invention, allow a user to select the strap length by cutting the appropriate portion off the reel. It should be noted that cutting an excessively long strap of the prior art (with only one aperture) down to size would result in a wasted portion of strap (without an aperture), a result avoided by the present invention. It should also be noted that considerable manufacturing cost may be saved using the configuration of FIG. 25, for the reel, in that a relatively infrequent die cut will be able to make the aperture and the thin section. This arrangement embodies herein the continuous-strap system wherein such continuous length of material comprises an aperture adjacent to at least one end portion of each such alternating wider width.

FIG. 29 also shows how an alternating wide cross section 208 and narrow cross section 209 can be patterned to form a preferred material-saving economical layout from a sheet of material 212, to reduce manufacturing costs. This layout preserves fastener material and minimizes manufacturing costs.

It is noted that the present invention, in a described embodiment, provides a simple dispensing mechanism for dispensing straps of variable length determined by the end user, having been preferably provided the material, preferably precut by a manufacturer (to provide such advantages). Preferably, the strip is composed of a hook and loop material or similarly constructed reversible fastener material, with fasteners on each side capable of mating with the other. Preferably, this material would be provided in a standard self-fastened coiled manner for storage or a dispenser. Preferably, the strips may be manufactured using sheet material with dies that create straps with at least one aperture or perforated apertures per wide strap segment interconnected by a more narrow linking segment. Preferably, a single strap with at least two ends and two apertures with substantial spacing in between the apertures may be cut along the length of the strip in between two apertures to create at least two new straps with two free ends.

Preferably, for this preferred embodiment of the present invention, the strips have multiple apertures. Preferably, the strips have perforated apertures. Preferably, the apertures are distributed per wide segments interconnected by a narrower linking segment. Preferably, varying the position of the cut will allow the user to tailor the sizing of the straps to the user's needs while achieving economical material-saving advantages. Significant variations of length, shape, design, economy and function may be achieved by a single easily-performed cut of the material by a standard cutting instrument. Preferably, this may include a pair of scissors, knife or cutting blade. The straps may have substantially similar strengths and would preferably not be weakened by perforations.

Preferably, the strips are die cut. Preferably, the strips are rotary cut from sheets of the reversible material. The straps may be formed in single arrays from a single sheet of strap material. The straps may be formed in adjacent arrays from a single sheet of strap material. Preferably, the straps may be formed in a nested pattern, for economical manufacturing. Preferably, the straps may be formed from an interlocking pattern, for economical manufacturing. Preferably, the material is provided in a roll. Preferably, the roll is part of a dispenser. Preferably, the dispenser utilizes a cutting mechanism.

Preferably, the material is provided in a coiled roll. Preferably, the material is provided in a coiled roll of a single strap, preferably with multiple apertures. Preferably, the roll may be unwound to a desired length and the strap may be cut between apertures to form a new strap of a desired length. The strap formed would in such cases have the strap anchoring, bundling and fastening advantages described above, including those given by having two independently operable arms.

For example, if the user had a six-foot strap of a uniform maximal width rolled in a coil with five apertures equally spaced at 12 inches apart, the user could choose to cut the material 18 inches from a first end to create a second two-armed strap that would have one end about six inches long and the other end about 12 inches long. The remaining roll would be a first strap with four apertures and of a total length of 4.5 feet. The user could then cut 9 inches from the shortened tip of the first roll to create a third double-armed strap that had arm dimensions of 3 inches and 6 inches. The shortened first strap would now be 3.75 feet in length. The large first strap might, for example, organize a garden hose system; the second strap might, for example, organize a laptop power cord; and the small third strap might, for example, organize wires in an electrical panel.

From the foregoing discussion, it is seen that, if a user wanted to fasten two objects, or sets of objects, together using the prior art fasteners, it would be necessary that the first set of objects be bundled first (set A), followed by the second set of objects (set B). Consequently, a drawback in the prior art is that, when using a single strap fastener (such as the GET A GRIP® strap), the set A objects cannot be cinched together well, as the fastened end of the GET A GRIP® strap is under the loop of the GET A GRIP® strap and the fingers tugging on the pulling end interfere with the fastening action of one layer on another. Thus, a bundled set of objects might not be bound as tightly as desired. Furthermore, the bundled set might become loose, slip, become repositioned, or even become undone. It is seen that the present invention provides a fastening strap system that permits tightly cinching the first set of objects to achieve a better total fit around all the bundled A and B sets of objects without this tendency to become undone.

It is further seen that, in the prior art, after the set A objects have been cinched together, with the set B objects then bundled to the set A objects, if a user only wanted to release the set A objects, the user would still be required to first release the set B objects from the fastening strap. Only then could the set A objects be released from the fastening strap. For example, assume that set A is a pair of ski poles and set B is a pair of skis. If a user bundled the ski poles together with a large fastening strap of the prior art, such as the configuration of the GET A GRIP® strap, the poles of set A would be in the center portion of the spiral wrapped GET A GRIP® strap. Next, the skis of set B would be bound within the outer wraps of the spiral wrapped GET A GRIP® strap. Now assume further that the user wants to free only the ski poles to loan to a friend. In this case, the user would first have to release the set B skis on the outer portion of the spiral wrapped bundle. This would be inconvenient and time consuming and leaves the second set B of the skis unbundled such that the skis might fall on the ground thus causing harm to someone's toes or causing the skis to be damaged by the impact on a non-snowy surface. Or, for example, the user might decide that the user wants to keep either the set B skis or the set A ski poles bundled by themselves and then attach that remaining bundled set to a third set C such as a car roof rack. It therefore would be desirable, as provided herein by the embodiments of the present invention, to have a fastening strap system that can fasten both a set A and a set B but then allow the release of either set A or set B while leaving the remaining set fastened intact, which could then be immediately attachable to a third set C.

Yet another example: A prior art hook and loop product for power cords has the plug end of a power cord secured through slits in the fastening strap, but only if the plug is properly dimensioned. If the plug is too large, the plug may not fit through the slits. If the plug is too small, then the plug will not be secured. Only if the plug is dimensioned correctly may the plug be secured through the slits of the strap and the remainder of the strap then used to bundle the remainder of the power cord. If the cord and plug are separately bundled, the same kinds of problems, as mentioned for the ski example using prior art devices, occur. This kind of problem is solved by the embodiments of this invention by providing a secure fastening strap that may release either of two fastened sets, i.e. the plug and the cord bundle, independently at will.

As another example, a pen and a pencil may be wrapped with a strip of ONE WRAP® material by winding one end of the strip around a free and easily manipulated pencil and then twirling the pencil around in consecutive spirals and then repeating the procedure to secure the other end of the strip around a pen. However, this procedure will not work if the user wants to secure the pencil to a desk drawer handle, because the desk would not twirl so easily. Also, if a handbag were secured to a desk drawer handle, the weight of the handbag might easily cause the spiraled material to become unwound as the force pulling the layers of materials apart is aligned in the same general direction as would normally occur to separate the fastening material layers, as discussed elsewhere herein. This invention, as shown and described, provides a fastening strap system for securing two items or sets of items together that allows separation of either set immediately with a minimum of manipulation while also maintaining a relatively strong fastening grip when fastened.

Some of the functional deficiencies of the prior art are that the strap must often be entirely unwound in order to attach the strap; one cannot, for example, keep one end of the strap coiled in a compact stored configuration and have only a small portion of only one end of the strap unwrapped and exposed to perform the anchoring function. This drawback becomes particularly important as the length of the strap increases. For example, as the length of the reversible fastening strap material increases there is more surface area and weight. The material tends to twist and turn and stick to itself more easily as there is more surface area and more chance the material is much more likely to fasten to itself prematurely and undesirably making it tangled and difficult to manage. This makes the threading process of the free end of a hook and loop strap and particularly a relatively long strap much more difficult, frustrating and time consuming. Also, another clear disadvantage of the prior art is that when using a relatively long strap, it will nearly always require two hands. For example, if the strap length is 36 inches (and therefore longer than the span of a hand between a thumb and two other gripping fingers), and a person was going to anchor the strap on an object, such as a ski pole, and then bundle skis, the person would need to secure the head region of a strap with one hand, stretch and straighten out the remaining entire length of the strap with a second hand, and then use the first hand to thread the tip though the aperture of the head region. Meanwhile, the person is trying to make sure the strap material does not twist and turn on itself, to tangle, fasten and interfere with this process. The present invention provides a self-fastening strap made of a self-fastening material, such as hook-and-loop material, that can be anchored with relative ease without having to unwind the entire strap or unbundle and unwind the entire strap, or with relatively less problems of tangling and prematurely self-fastening.

It is also noted that the present invention provides a self-fastening strap made of a self-fastening material, such as hook and loop material, that can be released without having to unwind the entire strap, or unbundle and unwind the entire strap, or that might be released easily from an anchored position with a single hand.

It is further noted that the present invention allows a user the choice to immediately fasten and selectively release only one of a multiple number, two or more, separate objects from the hook and loop fastening strap bundle. It provides for the selective and independent binding and release of multiple bundles of items from one another.

It is also noted that, while one might choose a material such as the self-fastening DUAL LOCK material made by 3M of St. Paul, Minn., or other similar one-sided self-fastening materials, this material is expensive, requires a press fit to activate the fastening and poorly adapts to apparel objects. [FIG. 21 shows an embodiment of the present invention using a "hook and hook" material like the above-mentioned one-sided self-fastening materials, but made by applicant as a two-sided material, with all the advantages set out hereinafter.] Furthermore, the goals are the fastening of two objects together while being able to immediately unfasten them. In addition, because the 3M™ material is only one-sided, a strap of such material cannot be merely folded back on itself at both ends to secure and fasten two objects together.

Also, depending on the density of the gripping appendages that are on the fastening side of the material, the surface might not fasten to itself. Thus, it is preferable to have a second side that has a second surface with different properties than the first surface, such as a second density of the gripping appendages or a different type of gripping appendage that allows the selection of a stronger or weaker fastening. Also, the mentioned 3M-company strap material does not have the soft pile of the hook surface of a hook and loop material strap. Under appropriate circumstances, it is preferable to have a strap with at least one self-fastening surface that has the ability to self engage and fasten a first set, while also having another surface with properties that might include immediate engagement on contact with the first surface, soft pile, or self-engagement with the same or different properties of the first.

In particular, a disadvantage of a single-sided self-fastening strap is that it does not permit a coiled bundling capability, as a coil of the single-sided self-fastening material does not attach to itself. Coiled bundling capability as provided by the present invention is desirable as sequential coiling of fastening surfaces adds increased fastening strength to subsequent wraps of double-sided fastening material.

In another usage example of a preferred double-sided strap, given a set of medical tubes, it would be desirable to have a double-sided fastening strap of self-fastening material such that, in a hospital environment, an IV (intravenous) tube could be connected to an IV pole, as is standard in hospitals for holding bags or bottles of IV fluid and their connections. In such an application of a double-sided strap, the material would preferably be wound around the IV pole in a substantially linearly aligned coil and be stored there in a neat arrangement. Also, when necessary, the coiled double-sided fastening strap would preferably be partially unwound and folded around or coiled around additional IV tubing. Additionally, when necessary, the additional IV tubing would preferably then be released from the fastening grip of the double-sided fastening strap of the present invention, or released from the IV pole, while maintaining the original IV tubing connected to the IV pole. Furthermore, the low particulate composition of the double-sided (non hook and loop) strap of the present invention would benefit clean room and surgical environments over some high particulate hook and loop materials.

FIG. 33 shows a plan view of a two-ended fastening strap, according to a preferred embodiment of the present invention. The embodiment of two-ended fastening strap 3300 (embodying herein a fastening strap system) shown in FIG. 33 is similar to the embodiment shown in FIG. 3 and FIG. 4.

As shown in FIG. 33, two-ended fastening strap 3300 preferably comprises a first strap portion 3303 and second strap portion 3306. The first strap portion preferably comprises first strap end portion 3303a, as shown. Further, first strap portion 3303 preferably comprises a first strap portion length and a first strap portion width, as shown. Similarly, second strap portion 3306 comprises second strap end portion 3306a, as shown. Second strap portion 3306 similarly comprises a second strap portion length and a second strap portion width, as shown.

Preferably, first strap portion 3303 and second strap portion 3306 are equal in terms of length, as shown. Upon reading the teachings of this specification, those with ordinary skill in the art will now understand that, under appropriate circumstances, considering such issues as cost, flexibility, ease in bundling, preventing unbundling, object accessibility, etc., other strap length arrangements, such as one strap being longer than the other strap portion, four strap portions, more than four strap portions, three strap portions, etc., may suffice.

Additionally preferably, first strap portion 3303 and second strap portion 3306 are equal in width, as shown. Upon reading the teachings of this specification, those with ordinary skill in the art will now understand that, under appropriate circumstances, considering such issues as size of items to be bundled, then-materials available, etc., other strap width arrangements such as one strap being wider than the other strap portion, multiple straps having multiple strap widths, etc., may suffice.

First strap portion 3303 and second strap portion are preferably "joined" at joining strap portion 3309, as shown. Preferably, two-ended fastening strap 3300 is a unitary piece of material, preferably flexible material (see FIG. 36 showing the flexibility of two-ended fastening strap 3300). Further, two-ended fastening strap 3300 preferably has first strap portion 3306 and second strap portion 3309 arranged opposite one another relative to joining strap portion 3309.

Preferably, two-ended fastening strap 3300 has a structure such that, when laid flat, a line drawn perpendicular to a longitudinal axis of first strap portion 3306 and passing through first strap portion 3306 does not pass through second strap portion 3309 (so long as the drawn line does not also pass through joining strap portion 3309). In such an arrangement, the strap ends (first strap end portion 3303a and second strap end portion 3306a) are opposite one another, as shown. Such "opposing" relationship provides the securing features described herein.

Upon reading the teachings of this specification, those with ordinary skill in the art will now understand that, under appropriate circumstances, considering such issues as cost, flexibility, ease in bundling, preventing unbundling, object accessibility, etc., other arrangements for straps, such as X-shaped strap arrangements extending from a central joining position, straps positioned at an angle relative to joining portion, straps in a "plus sign" configuration, etc., may suffice.

While applicant uses the words "joining strap" portion to described the "joining" of the first strap portion and second strap portion, it should be understood that applicant's two-ended fastening strap 3300 is preferably a continuous, unitary, single-piece element. Two-ended fastening strap 3300 exhibits the offset relationship described with respect to FIG. 3 and FIG. 4.

Preferably, joining strap portion 3309 has a width. Preferably, the width of joining strap portion 3309 is the widest portion of two-ended fastening strap 3300, as shown. The width of joining strap portion 3309 is preferably the combined width of first strap portion 3306 and second strap portion 3309.

With reference to FIG. 36, two-ended fastening strap 3300 preferably comprises two sides that are releasably fastenable or attachable to one another, as shown. Preferably, two-ended fastening strap 3300 comprises first side 3312 having a fastening surface thereon and second side 3316 also having a complementary fastening surface thereon. Preferably, one side of two-ended fastening strap 3300, such as first side 3312, comprises hook-type fasteners. Preferably, the other side of two-ended fastening strap 3300, such as second side 3316, comprises a complementary fastening surface to the hook-type fasteners. A complementary fastening surface to the hook-type fasteners is preferably a complementary hook-type fastener similar to that shown in FIG. 21 (showing a "hook and hook" material). Also preferably, a complementary fastening surface to the hook-type fasteners is preferably a complementary loop-type fastener.

Preferably, the entire surface of first side 3312 of two-ended fastening strap 3300 is covered with a fastenable surface. The entire surface of second side 3316 of two-ended fastening strap 3300 is preferably covered with a fastenable surface (preferably complementary to the fastenable surface of the first side).

FIG. 33 also illustrates the offset-relationship of two-ended fastening strap 3300 (which, again, is similar to the embodiment shown in FIG. 3).

Two-ended fastening strap 3300 preferably permits the bundling of two separate sets of items together (see FIG. 4). As shown in FIG. 4, the offset relationship provides the feature of allowing the secure bundling of a first set by first strap portion 3303 while also allowing the independent secure bundling of a second set by second strap portion 3306.

FIG. 36 further illustrates that two-ended fastening strap 3300 is preferably flexible and twistable so that the strap portions may loop around items to be bundled.

FIG. 34 shows a reel of continuous material having separable portions, according to a preferred embodiment of the present invention.

As shown in FIG. 34, two-ended fastening strap 3300 is preferably manufactured in an end-to-end fashion and preferably coiled to form reel 3400 (at least embodying herein at least one continuous length of material having separable portions) of continuous strap material wherein a user may selectively remove one or more of two-ended fastening strap 3300, when desired. Preferably, a user cuts a desired length of material from reel 3400. Preferably, reel 3400 of continuous strap material provides the user with flexibility by allowing a user to select the optimal length of the straps for each particular application. Preferably, reel 3400 has a plurality of two-ended fastening strap 3300 at regular intervals, as shown.

Preferably, a user cuts a length of the continuous strap material from the reel to expose a first strap portion and second strap portion creating a two-ended fastening strap as shown in FIG. 33. It is noted that a user may also select a "longer" piece of continuous strap material from reel 3400 in which the resulting piece has a first strap portion exposed, a section of multiple adjoining two-ended fastening straps 3300, and a second strap portion exposed. Preferably, users remove individual fastening straps, such as two-ended fastening strap 3300 shown in FIG. 33.

Preferably, reel 3400 comprises perforations or rip points between individual fastening straps wherein a user may easily tear away a fastening strap (a removable portion) from reel 3400.

FIG. 35 shows a plan view of a portion of the reel of FIG. 34. Each two-ended fastening strap 3300 is preferably separated by junction 3500, as shown. Junction 3500 is preferably a perforation or rip point, or, alternately preferably, an indication where the material may be cut (such arrangement at least embodying herein at least one separation assister). Preferably, users cut or tear away fastening straps from one another using junction 3500.

FIG. 36, as discussed above, shows a perspective view of the two-ended fastening strap of FIG. 33.

FIG. 37 shows a plan view of a fastening strap, according to another preferred embodiment of the present invention. The embodiment of fastening strap 3700 (embodying herein a fastening strap system) shown in FIG. 37 is similar to the embodiment shown in FIG. 6 through FIG. 9.

As shown in FIG. 37, fastening strap 3700 preferably comprises a first strap portion 3703 and second strap portion 3706. First strap portion 3703 preferably comprises first strap end portion 3703a, as shown. Further, first strap portion 3703 preferably comprises a first strap portion length and a first strap portion width, as shown. Similarly, second strap portion 3706 comprises second strap end portion 3706a, as shown. Second strap portion 3706 also comprises a second strap portion length and a second strap portion width, as shown.

Preferably, first strap portion 3703 and second strap portion 3706 are equal in terms of length, as shown. Upon reading the teachings of this specification, those with ordinary skill in the art will now understand that, under appropriate circumstances, considering such issues as size of items to be bundled, then-materials available, etc., other strap length arrangements such as one strap being longer than the other strap portion, four strap portions, more than four strap portions, three strap portions, etc., may suffice.

Additionally, first strap portion 3703 and second strap portion 3706 are preferably equal in terms of width, as shown. Upon reading the teachings of this specification, those with ordinary skill in the art will now understand that, under appropriate circumstances, considering such issues as size of items to be bundled, then-materials available, etc., other strap width arrangements such as one strap being wider than the other strap portion, multiple strap portions, etc., may suffice.

First strap portion 3703 and second strap portion are preferably "joined" via joining strap portion 3709, as shown. Preferably, fastening strap 3700 is a continuous, unitary piece of material, preferably flexible material (see FIG. 40).

Preferably, joining strap portion 3709 has a width, as shown. Preferably, width of joining strap portion 3709 is the widest portion of fastening strap 3700, as shown. The width of joining strap portion 3709 is preferably the combined widths of first strap portion 3703 and second strap portion 3706. Upon reading the teachings of this specification, those with ordinary skill in the art will now understand that, under appropriate circumstances, considering such issues as desired items to be bundled, handling issues, etc., other dimensions of joining strap portion, such as tapered widths, multiple widths, etc., may suffice.

Preferably, fastening strap 3700 has a structure such that, when laid flat, a line drawn perpendicular to a longitudinal axis of first strap portion 3703 and passing through first strap portion 3703 also passes through second strap portion 3306 (so long as the drawn line does not also pass through joining strap portion 3709). In such an arrangement, the strap ends (first strap end portion 3703a and second strap end portion 3706a) are on the same side of joining strap portion 3709, as shown. Such "opposing" relationship provides the securing features described herein.

With reference to FIG. 40, fastening strap 3700 preferably comprises two sides that are releasably fastenable or attachable to one another, as shown. Preferably, fastening strap 3700 comprises first side 3712 having a fastening surface thereon and second side 3716 also having a fastening surface thereon. Preferably, one side of fastening strap 3700, such as first side 3712, comprises hook-type fasteners. Preferably, the other side of fastening strap 3700, such as second side 3716, comprises a complementary fastening surface to the hook-type fasteners. A complementary fastening surface to the hook-type fasteners is preferably a complementary hook-type fastener similar to that shown in FIG. 21 (showing a "hook and hook" material). Also preferably, a complementary fastening surface to the hook-type fasteners is preferably a complementary loop-type fastener.

Preferably, the entire surface of first side 3712 of fastening strap 3700 is covered with a fastenable surface (preferably a hook or loop surface). Also preferably, the entire surface of second side 3716 of fastening strap 3700 is covered with a fastenable surface (preferably a complementary hook surface or a complementary loop surface). FIG. 40 further illustrates that fastening strap 3700 is preferably flexible and twistable.

FIG. 37 also the parallel-relationship of fastening strap 3700. Preferably, the parallel-relationship fastening strap 3700 comprises two parallel ends 3703a and 3703b. Fastening strap 3700 preferably loops to encircle items as shown in FIGS. 7 and 8.

FIG. 38 shows a reel of continuous material having separable portions, according to another preferred embodiment of the present invention.

As shown in FIG. 38, fastening strap 3700 is preferably manufactured in an end-to-end fashion and preferably coiled to form reel 3800 of continuous strap material wherein a user may selectively remove one or more of fastening strap 3700, when desired. Preferably, a user cuts a desired length of fastening strap material from reel 3800. Preferably, reel 3800 of continuous strap material provides the user with flexibility by allowing a user to select the optimal length of the strap material for each particular application. Preferably, reel 3800 has a plurality fastening strap 3700 at regular intervals, as shown. Preferably, a user cuts a length of the continuous strap material to expose a fastening strap (similar to that shown in FIG. 37). Preferably, users remove individual fastening straps 3700 from reel 3800. Reel 3800 preferably comprises perforations or rip points between individual fastening straps wherein a user may easily tear away a fastening strap from reel 3800.

FIG. 39 shows a plan view of a portion of the reel of FIG. 38. Preferably, each fastening strap 3700 is separated by junction 3900, as shown. Users preferably cut or preferably tear away fastening straps from one another using junction 3900. Further, the straps of fastening strap 3700 may be preferably separated by cutting or tearing at junction 3903 (junction between straps), as show.

FIG. 40, discussed above, shows a perspective view of the fastening strap of FIG. 37.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. A method of using a strap system to secure at least one first longitudinal element and at least one second longitudinal element, the method comprising the steps of:
   a) providing at least one fastening strap system with a base, the fastening strap system comprising
      i) at least one first elongated strap portion comprising
         (1) at least one first strap end portion extending inseparably from the base and
         (2) at least one first strap width, and
      ii) at least one second elongated strap portion comprising
         (1) at least one second strap end portion extending inseparably from the base, wherein the at least one first strap end portion and the at least one second strap end portion are divided and offset in parallel from each other, and
         (2) at least one second strap width,
      iii) wherein the fastening strap system consists of a unitary portion of flexible sheet material,
      iv) wherein the unitary portion of flexible sheet material comprises
         (1) at least one first side comprising at least one first fastening surface and
         (2) at least one second side comprising at least one second fastening surface adapted to be detachably fastenable to the at least one first fastening surface,
      v) wherein the second elongated strap portion is offset parallel from such first elongated strap portion a distance about equal to the at least one first strap width, and
      vi) wherein all the at least one first elongated strap portions and all the at least one second elongated strap portions are parallel;
   b) folding the at least one first elongated strap portion around the at least one first longitudinal element;
   c) folding the at least one second elongated strap portion around the at least one second longitudinal element;
   d) cinching the at least one first elongated strap portion; and
   e) cinching the at least one second elongated strap portion.

2. The method, according to claim 1, wherein:
   a) the step of folding the at least one first elongated strap portion around the at least one first longitudinal element comprises the step of looping the at least one first elongated strap portion clockwise around the at least one first longitudinal element; and
   b) the step of folding the at least one second elongated strap portion around the at least one second longitudinal element comprises the step of looping the at least one second elongated strap portion counter-clockwise around the at least one second longitudinal element.

3. The method, according to claim 1 wherein:
   a) the step of folding the at least one first elongated strap portion around the at least one first longitudinal element comprises
      i) creating at least one first loop around the at least one first longitudinal element comprising
         (1) folding, in a clockwise direction, the at least one first elongated strap portion around the at least one first longitudinal element and
         (2) cinching the at least one first elongated strap portion; and
   b) the step of folding the at least one second elongated strap portion around the at least one second longitudinal element comprises
      i) creating at least one second loop around the at least one second longitudinal element, wherein said at least one second loop is offset from said at least one first loop by a distance about equal to the at least one first strap width,
      ii) folding, in a counterclockwise direction, the at least one second elongated strap portion around the at least one second longitudinal element, and
      iii) cinching the at least one second elongated strap portion.

4. A strap system comprising:
   a) a first plurality of detachable fasteners;
   b) at least one first detachable-fastener strap structured and arranged to hold said first plurality of detachable fasteners, wherein the at least one first detachable-fastener surface comprises a free end extending inseparably from a base;
   c) a second plurality of detachable fasteners; and
   d) at least one second detachable-fastener strap structured and arranged to hold said second plurality of detachable fasteners, wherein the at least one second detachable-fastener strap comprises a free end extending inseparably from the base, wherein the first detachable-fastener strap free end and the second detachable-fastener strap free end are divided and offset in parallel from each other;
   e) wherein said at least one first detachable-fastener strap and said at least one second detachable-fastener strap comprise at least one unitary portion of flexible sheet material;
   f) wherein said at least one first detachable-fastener strap and said at least one second detachable-fastener strap are on different sides of said at least one unitary portion of flexible sheet material; and
   g) wherein said first plurality of detachable fasteners comprises at least one three-dimensional mushroom geometry.

5. The strap system according to claim 4 wherein said second plurality of detachable fasteners comprises at least one three-dimensional mushroom geometry.

6. The strap system according to claim 4 wherein said at least one second detachable-fastener strap is adapted to be detachably fastenable to said at least one first detachable-fastener strap.

7. The strap system according to claim 6 wherein said second plurality of detachable fasteners comprises loops.

8. The strap system according to claim 6 wherein said second plurality of detachable fasteners comprises hook fasteners.

9. The strap system according to claim 8 wherein said second plurality of detachable fasteners comprises mushroom-shaped hook fasteners.

10. A strap system comprising:
    a) a first plurality of detachable fasteners;
    b) at least one first detachable-fastener strap structured and arranged to hold said first plurality of detachable fasteners, wherein the at least one first detachable-fastener strap comprises a free end extending inseparably from a base;

c) a second plurality of detachable fasteners; and
d) at least one second detachable-fastener strap structured and arranged to hold said second plurality of detachable fasteners, wherein the at least one second detachable-fastener strap comprises a free end extending inseparably from the base, wherein the first detachable-fastener strap free end and the second detachable-fastener strap free end are divided and offset in parallel from each other;
e) wherein said at least one first detachable-fastener strap and said at least one second detachable-fastener strap comprise at least one unitary portion of flexible sheet material;
f) wherein said at least one first detachable-fastener strap and said at least one second detachable-fastener strap are on different sides of said at least one unitary portion of flexible sheet material; and
g) wherein said first plurality of detachable fasteners comprises at least one bio-absorbable material.

11. The strap system according to claim 10 wherein said second plurality of detachable fasteners comprises hook fasteners.

12. The strap system according to claim 11 wherein said second plurality of detachable fasteners comprises mushroom-shaped hook fasteners.

13. The strap system according to claim 12 wherein said first plurality of detachable fasteners comprises hook fasteners.

14. The strap system according to claim 13 wherein said at least one second detachable-fastener strap is adapted to be detachably fastenable to said at least one first detachable-fastener strap.

15. The strap system according to claim 10 wherein said at least one second detachable-fastener strap is adapted to be detachably fastenable to said at least one first detachable-fastener strap.

16. The strap system according to claim 10 wherein said at least one bio-absorbable material comprises polylactic acid.

* * * * *